(12) United States Patent
Imperial et al.

(10) Patent No.: US 9,062,118 B2
(45) Date of Patent: Jun. 23, 2015

(54) J-SUPERFAMILY CONOTOXIN PEPTIDES

(75) Inventors: Julita S. Imperial, Midvale, UT (US); Baldomero M. Olivera, Salt Lake City, UT (US); Paul F. Alewood, Queensland (AU); Heinz Terlau, Eckernfoerde (DE); David J. Craik, Queensland (AU); Estuardo Lopez-Vera, Salt Lake City, UT (US); Pradip K. Bandyopadhyay, Salt Lake City, UT (US)

(73) Assignees: University of Utah Research Foundation, Salt Lake City, UT (US); The University of Queensland, Brisbane, Queensland (AU); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 1681 days.

(21) Appl. No.: 12/301,827

(22) PCT Filed: Jun. 6, 2007

(86) PCT No.: PCT/US2007/013302
§ 371 (c)(1),
(2), (4) Date: Dec. 6, 2010

(87) PCT Pub. No.: WO2007/145987
PCT Pub. Date: Dec. 21, 2007

(65) Prior Publication Data
US 2011/0064668 A1    Mar. 17, 2011

Related U.S. Application Data

(60) Provisional application No. 60/811,092, filed on Jun. 6, 2006.

(51) Int. Cl.
A61K 38/00    (2006.01)
C07K 14/435    (2006.01)

(52) U.S. Cl.
CPC .......... *C07K 14/43504* (2013.01); *A61K 38/00* (2013.01)

(58) Field of Classification Search
None
See application file for complete search history.

(56) References Cited

PUBLICATIONS

Terlau, H. et al., "*Conus* Venoms: A Rich Source of Novel Ion Channel-Targeted Peptides," Physiol. Rev., vol. 84, pp. 41-68, © 2004 The American Physiological Society.
International Search Report and Written Opinion, PCT/US07/13302, filling date: Jun. 6, 2007, mail date: Sep. 9, 2008, The University of Utah Research Foundation.
Terlau, H. et al., "*Conus* Venoms: A Rich Source of Novel Ion Channel-Targeted Peptides," Physiol. Rev., 2004, vol. 84, pp. 41-68.
International Search Report dated Sep. 9, 2008, PCT/US07/13302, Applicant: University of Utah Research Foundation, 8 pages.

*Primary Examiner* — Karlheinz R Skowronek
*Assistant Examiner* — Roy Teller
(74) *Attorney, Agent, or Firm* — Rothwell, Figg, Ernst & Manbeck P.C.

(57) ABSTRACT

The invention relates to relatively short peptides (termed J-Superfamily conotoxin peptides, J-conotoxins or J-conotoxin peptides herein), about 25 residues in length, which are naturally available in minute amounts in the venom of the cone snails or analogous to the naturally available peptides, and which preferably include two disulfide bonds. The J-conotoxins are useful for treating disorders involving voltage gated ion channels and/or receptors.

15 Claims, 12 Drawing Sheets

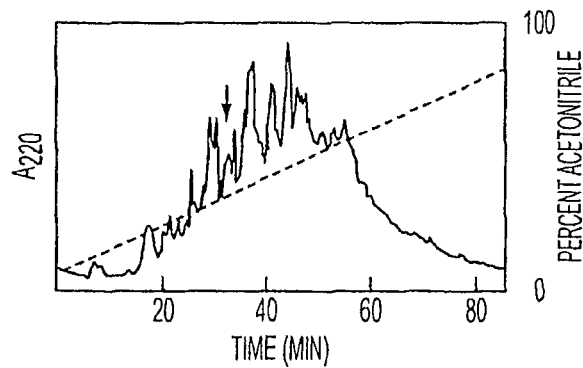
FIG. 1A
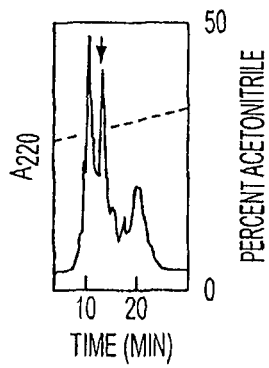
FIG. 1B
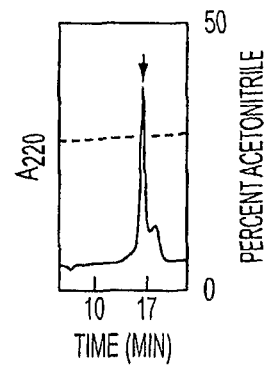
FIG. 1C
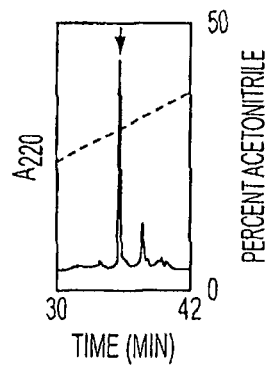
FIG. 1D
FPRPRICNLACRAGIGHKYPFCHCR-NH₂
FIG. 2A
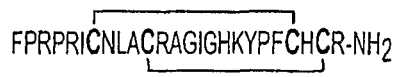
| 5-5 MOTIF | SUPERFAMILY |
|---|---|
| CC-C-C | A |
| CC-CC | T |
| C-C-C-C | J |
FIG. 2B

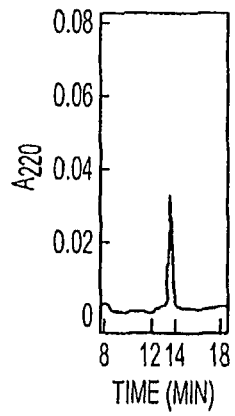 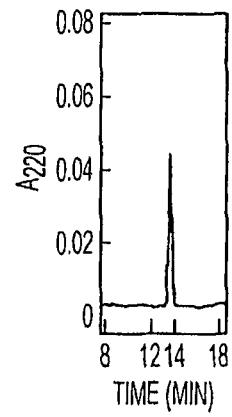 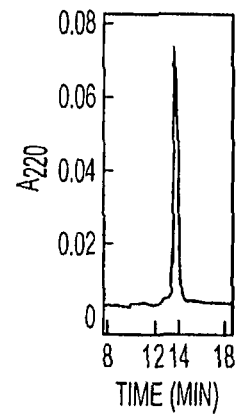
FIG. 3A　　　FIG. 3B　　　FIG. 3C
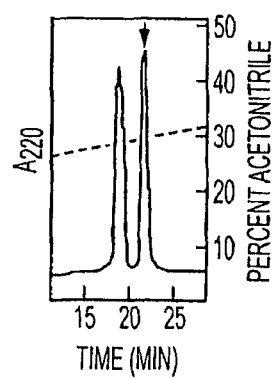 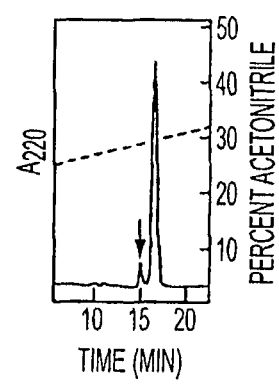
FIG. 4A　　　FIG. 4B

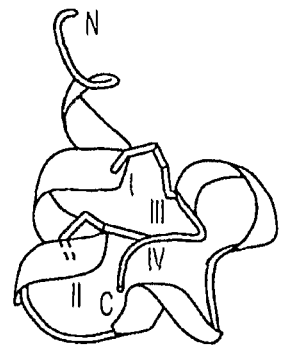
FIG. 5A　　　　　　　　　　FIG. 5B
FIG. 6A
```
pl14a   FPRPRICNLACRAGIGHKYPFCHCR-NH2
pl14.1  GPGSAICNMACRLGQGHMYPFCNCN-NH2
pl14.2  GPGSAICNMACRLEHGHLYPFCHCR-NH2
pl14.3  GPGSAICNMACRLEHGHLYPFCNCD-NH2
fe14.1  SPGSTICKMACRTGNGHKYPFCNCR-NH2
fe14.2  SSGSTVCKMMCRLGYGHLYPSCGCR-NH2
```
FIG. 6B

US 9,062,118 B2

J-SUPERFAMILY CONOTOXIN PEPTIDES

CROSS-REFERENCE TO RELATED APPLICATIONS

The present application is a national stage filing under 35 U.S.C. §371 of PCT/US2007/013302, filed on 6 Jun. 2007 which in turn claims priority under 35 U.S.C. §119(e) to U.S. provisional patent application Ser. No. 60/811,092 filed 6 Jun. 2006, incorporated herein by reference.

REFERENCE TO GOVERNMENT SUPPORT

This invention was made with government support under GM048667 awarded by National Institutes of Health. The government has certain rights in the invention.

BACKGROUND OF THE INVENTION

The invention relates to relatively short peptides (termed J-Superfamily conotoxin peptides, J-conotoxins or J-conotoxin peptides herein), about 25 residues in length, which are naturally available in minute amounts in the venom of the cone snails or analogous to the naturally available peptides, and which preferably include two disulfide bonds.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

*Conus* is a genus of predatory marine gastropods (snails) which envenomate their prey. Venomous cone snails use a highly developed apparatus to deliver their cocktail of toxic conotoxins into their prey. In fish-eating species such as *Conus magus* the cone detects the presence of the fish using chemosensors in its siphon. When close enough the cone extends its proboscis and impales the fish with a hollow harpoon-like tooth containing venom. This immobilizes the fish and enables the cone snail to wind it into its mouth via the tooth held at the end of its proboscis. For general information on *Conus* and their venom see the website address "grimwade.biochem" at "unimelb.edu.au". Prey capture is accomplished through a sophisticated arsenal of peptides which target specific ion channel and receptor subtypes. Each *Conus* species venom appears to contain a unique set of 50-200 peptides. The composition of the venom differs greatly between species and between individual snails within each species, each optimally evolved to paralyse the snail's prey.

Conopeptides, typically 12-30 amino acid residues in length, are the active peptidic components in cone snail venoms, and these are classified into two major groups. One group consists of disulfide-rich peptides commonly termed conotoxins; the second group comprises peptides with only one disulfide bond or none. The cysteine-rich conotoxins are encoded by genes that share significant sequence similarity within superfamilies. Conotoxins that belong to the same gene superfamily share a characteristic disulfide pattern and a general pharmacological targeting specificity (Terlau et al., 2004).

The venoms consist of a large number of different peptide components that when separated exhibit a range of biological activities: when injected into mice they elicit a range of physiological responses from shaking to depression. The paralytic components of the venom that have been the focus of recent investigation are the α-, ω- and μ-conotoxins. All of these conotoxins act by preventing neuronal communication, but each targets a different aspect of the process to achieve this. The α-conotoxins target nicotinic ligand gated channels, the μ-conotoxins target the voltage-gated sodium channels and the ω-conotoxins target the voltage-gated calcium channels (Olivera et al., 1985). For example a linkage has been established between α-, αA- & ψ-conotoxins and the nicotinic ligand-gated ion channel; ω-conotoxins and the voltage-gated calcium channel; μ-conotoxins and the voltage-gated sodium channel; δ-conotoxins and the voltage-gated sodium channel; κ-conotoxins and the voltage-gated potassium channel; conantokins and the ligand-gated glutamate (NMDA) channel. For a partial list of *Conus* peptides and their amino acid sequences see the website address "pir" at "georgetown.edu".

However, the structure and function of only a small minority of these peptides have been determined to date. For peptides where function has been determined, three classes of targets have been elucidated: voltage-gated ion channels; ligand-gated ion channels, and G-protein-linked receptors.

*Conus* peptides which target voltage-gated ion channels include those, that delay the inactivation of sodium channels, as well as blockers specific for sodium channels, calcium channels and potassium channels. Peptides that target ligand-gated ion channels include antagonists of NMDA and serotonin receptors, as well as competitive and noncompetitive nicotinic receptor antagonists. Peptides which act on G-protein receptors include neurotensin and vasopressin receptor agonists. The unprecedented pharmaceutical selectivity of conotoxins is at least in part defined by specific disulfide bond frameworks combined with hypervariable amino acids within disulfide loops (for a review see McIntosh et al., 1998).

Due to the high potency and exquisite selectivity of the conopeptides, several are in various stages of clinical development for treatment of human disorders. For example, two *Conus* peptides are being developed for the treatment of pain. The most advanced is ω-conotoxin MVIIA (ziconotide), an N-type calcium channel blocker (see Heading, C., 1999; U.S. Pat. No. 5,859,186). ω-Conotoxin MVIIA, isolated from *Conus magus*, is approximately 1000 times more potent than morphine, yet does not produce the tolerance or addictive properties of opiates. ω-Conotoxin MVIIA has completed Phase III (final stages) of human clinical trials and is now awaiting U.S. Food and Drug Administration approval as a therapeutic agent. ω-Conotoxin MVIIA is introduced into human patients by means of an implantable, programmable pump with a catheter threaded into the intrathecal space. Preclinical testing for use in post-surgical pain is being carried out on another *Conus* peptide, contulakin-G, isolated from *Conus geographus* (Craig et al. 1999). Contulakin-G is a 16 amino acid O-linked glycopeptide whose C-terminus resembles neurotensin. It is an agonist of neurotensin receptors, but appears significantly more potent than neurotensin in inhibiting pain in in vivo assays.

In view of a large number of biologically active substances in *Conus* species it is desirable to further characterize them and to identify peptides capable of treating disorders involving voltage-gated ion channels, ligand-gated ion channels and/or receptors. Surprisingly, and in accordance with this invention, Applicants have discovered novel conotoxins that can be useful for the treatment of disorders involving voltage-gated ion channels, ligand-gated ion channels and/or receptors and could address a long felt need for a safe and effective treatment.

SUMMARY OF THE INVENTION

The invention relates to relatively short peptides (termed J-Superfamily conotoxin peptides, J-conotoxins or J-conotoxin peptides herein), about 25 residues in length, which are naturally available in minute amounts in the venom of the cone snails or analogous to the naturally available peptides, and which preferably include two disulfide bonds.

More specifically, the present invention is directed to J-conotoxin peptides having the general formula I:

(SEQ ID NO: 1)
Xaa1-Xaa2-Xaa3-Xaa4-Xaa5-Xaa6-Cys-Xaa7-Xaa8-Xaa9-

Cys-Xaa10-Xaa11-Xaa12-Xaa13-Xaa14-Xaa15-Xaa16-

Xaa17-Xaa18-Xaa19-Cys-Xaa20-Cys-Xaa21, wherein Xaa1 is Phe, Gly, Ser, Thr, g-Ser (where g is glycosylation), g-Thr or any synthetic hydroxylated amino acid; Xaa2 is Pro, hydroxy-Pro (Hyp), Ser, Thr, g-Ser, g-Thr or any synthetic hydroxylated amino acid; Xaa3 is Gly, Arg, Lys, ornithine, homo-Lys, homoarginine, nor-Lys, N-methyl-Lys, N,N'-dimethyl-Lys, N,N',N"-trimethyl-Lys or any synthetic basic amino acid; Xaa4 is Pro, hydroxy-Pro (Hyp), Ser, Thr, g-Ser, g-Thr or any synthetic hydroxylated amino acid; Xaa5 is Ala, Thr, g-Thr, Ser, g-Ser, any synthetic hydroxylated amino acid, Arg, Lys, ornithine, homo-Lys, homoarginine, nor-Lys, N-methyl-Lys, N,N'-dimethyl-Lys, N,N',N"-trimethyl-Lys or any synthetic basic amino acid; Xaa6 is an aliphatic amino acid bearing linear or branched saturated hydrocarbon chains such as Leu (D or L), Ile and Val or non-natural derivatives of the aliphatic amino acid; Xaa7 is Asn, Gln, Lys, Arg, ornithine, homo-Lys, homoarginine, nor-Lys, N-methyl-Lys, N,N'-dimethyl-Lys, N,N',N"-trimethyl-Lys or any synthetic basic amino acid; Xaa8 is Met, an aliphatic amino acid bearing linear or branched saturated hydrocarbon chains such as Leu (D or L), Ile and Val or non-natural derivatives of the aliphatic amino acid; Xaa9 is Ala or Met; Xaa10 is Arg, Lys, ornithine, homo-Lys, homoarginine, nor-Lys, N-methyl-Lys, N,N'-dimethyl-Lys, N,N',N"-trimethyl-Lys or any synthetic basic amino acid; Xaa11 is Ala, Thr, g-Thr, Ser, g-Ser, any synthetic hydroxylated amino acid, an aliphatic amino acid bearing linear or branched saturated hydrocarbon chains such as Leu (D or L), Ile and Val or non-natural derivatives of the aliphatic amino acid; Xaa12 is Gly, Glu, Asp or any synthetic acidic amino acid; Xaa13 is Gln, Asn, His, Tyr, meta-Tyr, ortho-Tyr, nor-Tyr, mono-halo-Tyr, di-halo-Tyr, O-sulpho-Tyr, O-phospho-Tyr, nitro-Tyr, an aliphatic amino acids bearing linear or branched saturated hydrocarbon chains such as Leu (D or L), Ile and Val or non-natural derivatives of the aliphatic amino acid; Xaa14 is Gly; Xaa15 is His; Xaa16 is Met, Lys, Arg, ornithine, homo-Lys, homoarginine, nor-Lys, N-methyl-Lys, N,N'-dimethyl-Lys, N,N',N"-trimethyl-Lys, any synthetic basic amino acid, an aliphatic amino acid bearing linear or branched saturated hydrocarbon chains such as Leu (D or L), Ile and Val or non-natural derivatives of the aliphatic amino acid; Xaa17 is Tyr, meta-Tyr, ortho-Tyr, nor-Tyr, mono-halo-Tyr, di-halo-Tyr, O-sulpho-Tyr, O-phospho-Tyr or nitro-Tyr; Xaa18 is Pro or Hyp; Xaa19 is Phe, Ser, Thr, g-Ser, g-Thr any synthetic hydroxylated amino acid; Xaa20 is His, Gly, Asn or Gln; and Xaa21 is Asn, Gln, Glu, Gla, Asp, any synthetic acidic amino acid, Arg, Lys, ornithine, homo-Lys, homoarginine, nor-Lys, N-methyl-Lys, N,N'-dimethyl-Lys, N,N',N"-trimethyl-Lys or any synthetic basic amino acid.

The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic amino acid, e.g., tetrazolyl derivatives of Gly and Ala. The nonnatural derivatives of the aliphatic amino acids include those synthetic derivatives bearing non-natural aliphatic branched or linear side chains $C_nH_{2n+2}$ up to and including n=8. The Met residues may be substituted with norleucine (Nle). The halogen is iodo, chloro, fluoro or bromo; preferably iodo for halogen substituted-Tyr and bromo for halogen-substituted Trp.

The present invention is also directed to novel specific J-conotoxin peptides within general formula I having the mature toxin sequences set forth in Table 1.

TABLE 1

| J-Superfamily Conotoxin Peptides | |
|---|---|
| FX3RX3RICNLACRAGIGHKX5X3FCHCR# | (SEQ ID NO: 2) |
| GX3GSAICNMACRLGQGHMX5X3FCNCN# | (SEQ ID NO: 3) |
| GX3GSAICNMACRLX1HGHLX5X3FCHCR# | (SEQ ID NO: 4) |
| GX3GSAICNMACRLXIHGHLX5X3FCNCD# | (SEQ ID NO: 5) |
| SX3GSTICKMACRTGNGHKX5X3FCNCR# | (SEQ ID NO: 6) |
| SSGSTVCKMMCRLGX5GHLX5X3SCGCR# | (SEQ ID NO: 7) |

Where
X1 is Glu or γ-carboxy-Glu
X2 is Gln or pyro-Glu
X3 is Pro or hydroxy-Pro
X4 is Trp or bromo-Trp
X5 is Tyr, $^{125}$I-Tyr, mono-iodo-Tyr, di-iodo-Tyr, O-sulpho-Tyr or O-phospho-Tyr
# is free carboxyl or amidated C-terminus, preferably amidated In addition, the present invention is directed to the above J-conotoxins in which the Arg residues may be substituted by Lys, ornithine, homoargine, nor-Lys, N-methyl-Lys, N,N-dimethyl-Lys, N,N,N-trimethyl-Lys or any synthetic basic amino acid; the Lys residues may be substituted by Arg, ornithine, homoargine, nor-Lys, or any synthetic basic amino acid; the Tyr residues may be substituted with any synthetic hydroxy containing amino acid; the Ser residues may be substituted with Thr or any synthetic hydroxylated amino acid; the Thr residues may be substituted with Ser or any synthetic hydroxylated amino acid; the Phe and Trp residues may be substituted with any synthetic aromatic amino acid; and the Asn, Ser, Thr or Hyp residues may be glycosylated. The Cys residues may be in D or L configuration and may optionally be substituted with homocysteine (D or L). The Tyr residues may also be substituted with the 3-hydroxyl or 2-hydroxyl isomers (meta-Tyr or ortho-Tyr, respectively) and corresponding O-sulpho- and O-phospho-derivatives. The acidic amino acid residues may be substituted with any synthetic acidic amino acid, e.g., tetrazolyl derivatives of Gly and Ala. The aliphatic amino acids may be substituted by synthetic derivatives bearing non-natural aliphatic branched or linear side chains $C_nH_{2n+2}$ up to and including n=8. The Leu residues may be substituted with Leu (D). The Glu residues may be substituted with Gla. The Gla residues may be substituted with Glu. The N-terminal Gln residues may be substituted with pyroGlu. The Met residues may be substituted with norleucine (Nle).

The present invention is further directed to derivatives of the above peptides and peptide derivatives which are acylic permutations in which the cyclic permutants retain the native bridging pattern of native toxin. See Craik et al. (2001).

Examples of synthetic aromatic amino acid include, but are not limited to, such as nitro-Phe, 4-substituted-Phe wherein the substituent is $C_1$-$C_3$ alkyl, carboxyl, hyrdroxymethyl, sulphomethyl, halo, phenyl, —CHO, —CN, —$SO_3H$ and —NHAc. Examples of synthetic hydroxy containing amino acid, include, but are not limited to, such as 4-hydroxymethyl-Phe, 4-hydroxyphenyl-Gly, 2,6-dimethyl-Tyr and 5-amino-Tyr. Examples of synthetic basic amino acids include, but are not limited to, N-1-(2-pyrazolinyl)-Arg, 2-(4-piperinyl)-Gly, 2-(4-piperinyl)-Ala, 2-[3-(2S)pyrrolininyl]-Gly and 2-[3-(2S)pyrrolininyl]-Ala. These and other synthetic basic amino acids, synthetic hydroxy containing amino acids or synthetic aromatic amino acids are described in Building Block Index, Version 3.0 (1999 Catalog, pages 4-47 for hydroxy containing amino acids and aromatic amino acids and pages 66-87 for basic amino acids; see also the website "amino-acids dot com"), incorporated herein by reference, by and available from RSP Amino Acid Analogues, Inc., Worcester, Mass. Examples of synthetic acid amino acids include those derivatives bearing acidic functionality, including carboxyl, phosphate, sulfonate and synthetic tetrazolyl derivatives such as described by Ornstein et al. (1993) and in U.S. Pat. No. 5,331,001, each incorporated herein by reference, and such as shown in the following schemes 1-3.

Scheme 1

FmocHN COOH

FmocHN COOH

R = COOH, tetazole, $CH_2COOH$, 4-$NHSO_2CH_3$, 4-$NHSO_2$Phenyl, 4-$CH_2SO_3H$, $SO_3H$, 4-$CH_2PO_3H_2$, $CH_2CH_2COOH$, $OCH_2$Tetrazole, $CH_2S$Tetrazole, HNTetrazole, $CONHSO_2R_1$ where $R_1$ is $CH_3$ or Phenyl, $SO_2$-Tetrazole, $CH_2CH_2SO_3H$, 1,2,3-tetrazole, 3-isoxazolone, amidotetrazole, $CH_2CH_2PO_3H_2$ Scheme 2

R = COOH, tetrazole, $CH_2COOH$, $CH_2$tetrazole

Scheme 3

FmocHN COOH

FmocHN COOH

R = COOH, tetazole, $CH_2COOH$, 4-$NHSO_2CH_3$, 4-$NHSO_2$Phenyl, 4-$CH_2SO_3H$, $SO_3H$, 4-$CH_2PO_3H_2$, $CH_2CH_2COOH$, $OCH_2$Tetrazole, $CH_2S$Tetrazole, HNTetrazole, $CONHSO_2R_1$ where $R_1$ is $CH_3$ or Phenyl, $SO_2$-Tetrazole, $CH_2CH_2SO_3H$, 1,2,4-tetrazole, 3-isoxazolone, amidotetrazole, $CH_2CH_2PO_3H_2$ n = 0, 1, 2, or 3

Optionally, in the peptides of general formula I and the specific peptides described above, the Asn residues may be modified to contain an N-glycan and the Ser, Thr and Hyp residues may be modified to contain an O-glycan (e.g., g-N, g-S, g-T and g-Hyp). In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The gylcan may also include similar polyhydroxy groups, such as D-penicillamine 2,5 and halogenated derivatives thereof or polypropylene glycol derivatives. The glycosidic linkage is β and 1-4 or 1-3, preferably 1-3. The linkage between the glycan and the amino acid may be α or β, preferably α and is 1-.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. Pat. No. 6,369,193 and in PCT Published Application No. WO 00/23092, each incorporated herein by reference. A preferred glycan is Gal(β1→3)GalNAc(α1→).

Optionally, in the peptides of general formula I and the specific peptides described above, pairs of Cys residues may be replaced pairwise with isoteric lactam or ester-thioether replacements, such as Ser/(Glu or Asp), Lys/(Glu or Asp), Cys/(Glu or Asp) or Cys/Ala combinations. Sequential coupling by known methods (Hargittai et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analogues.

The peptides of the general formula and the specific peptides disclosed herein contain 4 Cys residues leading to 2 disulfide bridges. The preferred disulfide bridging is as follows: Cys1-Cys3 and Cys2-Cys4, wherein Cys1 refers to the first Cys residue in the sequence of the J-Superfamily conotoxin peptides, Cys2 refers to the second Cys residue in the sequence of the J-Superfamily conotoxin peptides, etc.

The present invention is also directed to the identification of the nucleic acid sequences encoding these peptides and their propeptides and the identication of nucleic acid sequences of additional related J-conotoxin peptides. Thus, the present invention is directed to nucleic acids coding for the conotoxin peptide precursors (or conotoxin propeptides) set forth herein. The present invention is further directed to the conotoxin propeptides set forth herein.

The present invention is further directed to a method of treating disorders associated with voltage gated ion channel or receptor disorders in a subject comprising administering to the subject an effective amount of the pharmaceutical composition comprising a therapeutically effective amount of a J-conotoxin peptide described herein or a pharmaceutically acceptable salt or solvate thereof. The present invention is also directed to a pharmaceutical composition comprising a therapeutically effective amount of a J-conotoxin peptide described herein or a pharmaceutically acceptable salt or solvate thereof and a pharmaceutically acceptable carrier.

Another embodiment of the invention contemplates a method of identifying compounds that mimic the therapeutic activity of the instant peptide, comprising the steps of (a) conducting a biological assay on a test compound to determine the therapeutic activity; and (b) comparing the results obtained from the biological assay of the test compound to the results obtained from the biological assay of the peptide. In relation to radioligand probes of J-Superfamily conotoxins for screening of small molecules, acting at unique allosteric sites, synthesis of such screening tools is not restricted to radioiodinated tyrosine derivatives. Incorporation of standard commercially available tritiated amino acid residues can also be utilized.

BRIEF DESCRIPTION OF THE FIGURES

FIGS. 1A-1D show the isolation of pl14a from *C. planorbis* venom. The arrow in each HPLC run indicates the location of the fraction containing the peptide. All the elution buffers had 0.1% TFA. FIG. 1A: The venom extract was chromatographed in a preparative Vydac C18 column eluted with 4.5 to 90% acetonitrile. FIG. 1B: The peak containing the peptide in A was subfractionated using an analytical Vydac C18 column and an elution gradient of 28 to 34% acetonitrile. FIG. 1C: The fraction containing the peptide in B was further subfractionated using a gradient of 0.09% acetonitrile/min. FIG. 1D: The major peak in C was completely reduced and alkylated and then chromatographed in an analytical Vydac C18 column eluted with a gradient of 0.9% acetonitrile/min. The major peak yielded the sequence for pl14a.

FIGS. 2A-2B show peptide structure. FIG. 2A: Peptide sequence of pl14a showing the disulfide connectivity. FIG. 2B: Disulfide motifs found in conotoxin superfamilies with four cysteines.

FIGS. 3A-3C show coelution of native and synthetic preparations of pl14a. The HPLC runs were carried out using a gradient of 0.45% acetonitrile/min in 0.1% TFA: pl14a isolated from *C. planorbis* venom (FIG. 3A), synthetic pl14a (FIG. 3B), and a mixture of the native and synthetic samples of pl14a identical to those used in the individual runs (FIG. 3C).

FIGS. 4A-4B show partial reduction and alkylation of pl14a. FIG. 4A: The HPLC chromatogram after partial reduction shows the peak of the peptide with one disulfide bond cleaved (indicated by arrow) overlapping with the peak of the native peptide. The adjacent peak is that of the completely reduced pl14a. FIG. 4B: The HPLC profile of the alkylation reaction shows the separation of the partially alkylated p14a (indicated by arrow) from the native peptide.

FIGS. 5A-5B show the three-dimensional structure of pl14a. FIG. 5A: A superposition of the 20 lowest-energy structures of pl14a. FIG. 5B: A ribbon representation of the secondary structure of pl14a.

FIGS. 6A-6B show sequences in accordance with the present invention. FIG. 6A: pl14a clone. The arrows indicate the predicted cleavage sites between the signal sequence and the propeptide (arrow 1) using SignalP 3.0 Server and between the propeptide and the mature pl14a (arrow 2). The DNA sequence is SEQ ID NO:8. The propeptide sequence is SEQ ID NO:9. FIG. 6B: Homologous sequences identified from the cDNA of *C. planorbis* and *C. ferrugineus*. The sequences are as follows: pl14a: SEQ ID NO:10; pl14.1: SEQ ID NO:11; pl14.2: SEQ ID NO:12; pl14.3: SEQ ID NO:13; fe14.1: SEQ ID NO:14; and fe14.2: SEQ ID NO:15.

FIGS. 7A-7B show activity of pl14a in nAChR assays. FIG. 7A: pl14a was applied to oocytes expressing the nAChR subtypes at 3 μM for the muscle subtype ($\alpha 1\beta 1\epsilon\delta$) and at 10 μM for the neuronal subtype ($\alpha 3\beta 4$). Arrows indicate the first currents elicited after toxin equilibration for 5 min, by an ACh pulse of 1-10 μM for the muscle skeletal subtypes and 100 μM for the neuronal subtypes. pl14a at 3 μM blocked the elicited currents nearly completely in $\alpha 1\beta 1\epsilon\delta$, and the toxin dissociated rapidly from the receptor. A block of approximately 50% of the elicited current was obtained in $\alpha 3\beta 4$, with a similar dissociation rate. FIG. 7B: Dose-response curves for pl14a in each subtype. Each data point is the average of responses obtained from three oocytes, and the curves were generated using Prism. The $IC_{50}$ for the adult mouse muscle subtype is 0.54 μM, and the $IC_{50}$ for the rat $\alpha 3\beta 4$ neuronal subtype is 8.7 μM.

FIG. 8 shows that pl14a blocks Kv1.6 channels. (Left) Whole-cell currents obtained for depolarizing pulses to 0 mV from a holding potential of −100 mV from oocytes expressing different Kv1 channels. The bath solution was normal frog Ringer's solution. (Right) Addition of 1 μM pl14a had almost no effect for Kv1.1-Kv1.5-mediated currents, whereas Kv1.6-mediated currents are blocked by ~50%. The horizontal bars correspond to 50 ms and the vertical bars to 1 μA. Current records were low-pass-filtered at 1 kHz (−3 db) and sampled at 4 kHz.

FIG. 9 shows a phylogenetic tree (Bayesian estimate at 50% majority rule) of conotoxins in the J-superfamily, pl14a, pl14.1, pl14.2, pl14.3, fe14.1, and fe14.2 (this application), other conotoxins with the same cysteine pattern, flf14a and vil14a (Moller, 2005), and other Kv1 channel toxins, which include BgK (Cotton et al., 1997) from sea anemone and Ce1 (Olamendi-Portugal et al. 2005), ChTx (Miller, 1995), CoTx1 (Selisko, 1998), OsK2 (Dudina et al., 2001), Pi2 (Peter et al., 2001), and Tt28 (Abdel-Mottaleb et al., 2006) from scorpion. Scorpion toxin BmTx3 blocks both A-type K+ and HERG currents (Huys et al., 2004).

FIG. 10 shows the effect of 10 μM pl14a on the responses of neuronal nAChR subtypes expressed in oocytes compared to blank controls. The preparation of oocytes and the conditions used in the clamping experiments were as described in Materials and Methods.

FIGS. 11A and 11B show the solution structures of pl14a showing the potential diad (FIG. 11A) and a group of basic residues (FIG. 11B). The structures are rendered in RasMol stick format and Shapely colors.

FIG. 12 shows the HPLC profiles of absorbance at 220 nm for linear pl14aTrB (top), the oxidation reaction mixture of pl14aTrB (middle) after 20 h showing pl14aTrB folding isomer 1 (left peak) and pl14aTrB folding isomer 2 (right peak), and the combination of the two samples (bottom). The profiles were aligned at the injection peaks of the chromatograms.

Figure 16:
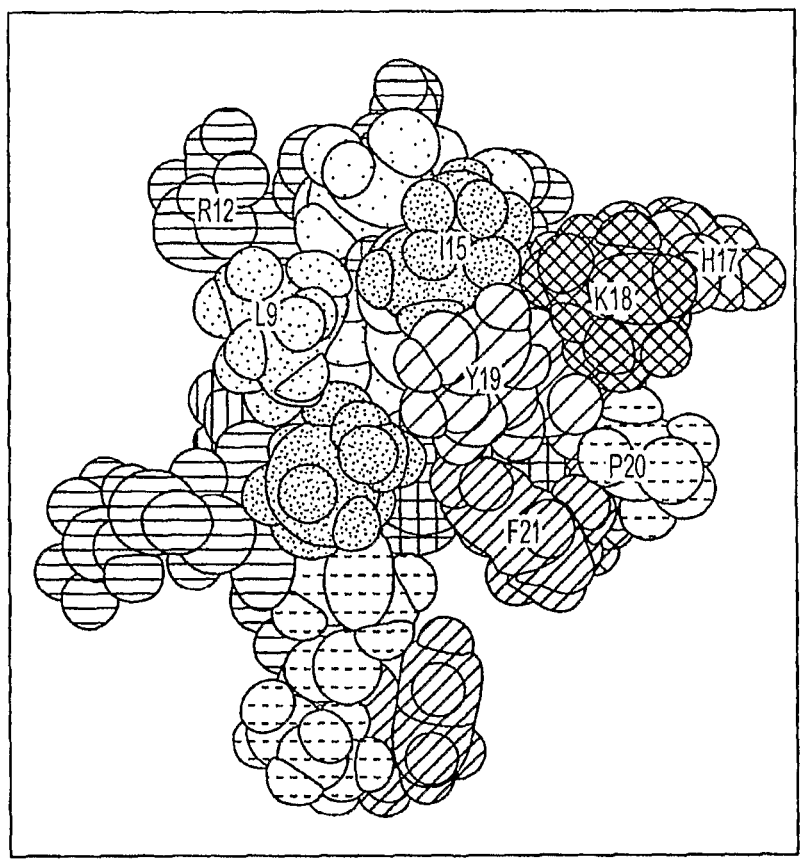

FIG. 16 shows the solution structure of p114a showing the relative roles of residues on activity of p114a on the α1β1εδ subtype of mouse muscle nAChR. The structure is rendered in RasMol spacefill format and Shapely colors. The residues adjacent to $K^{18}$ are labeled in yellow and the relatively distant residues are labeled in white.

Figure 17:
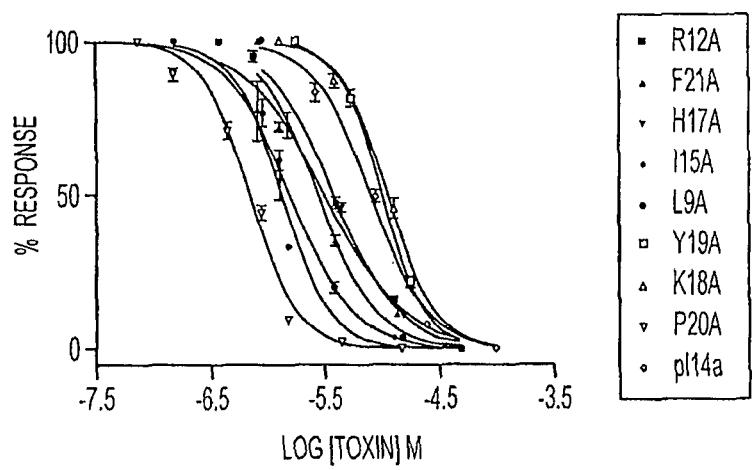

FIG. 17 shows the dose-response plots for p114a and alanine analogs on α3β4 subtype of nAChR.

Figure 18:
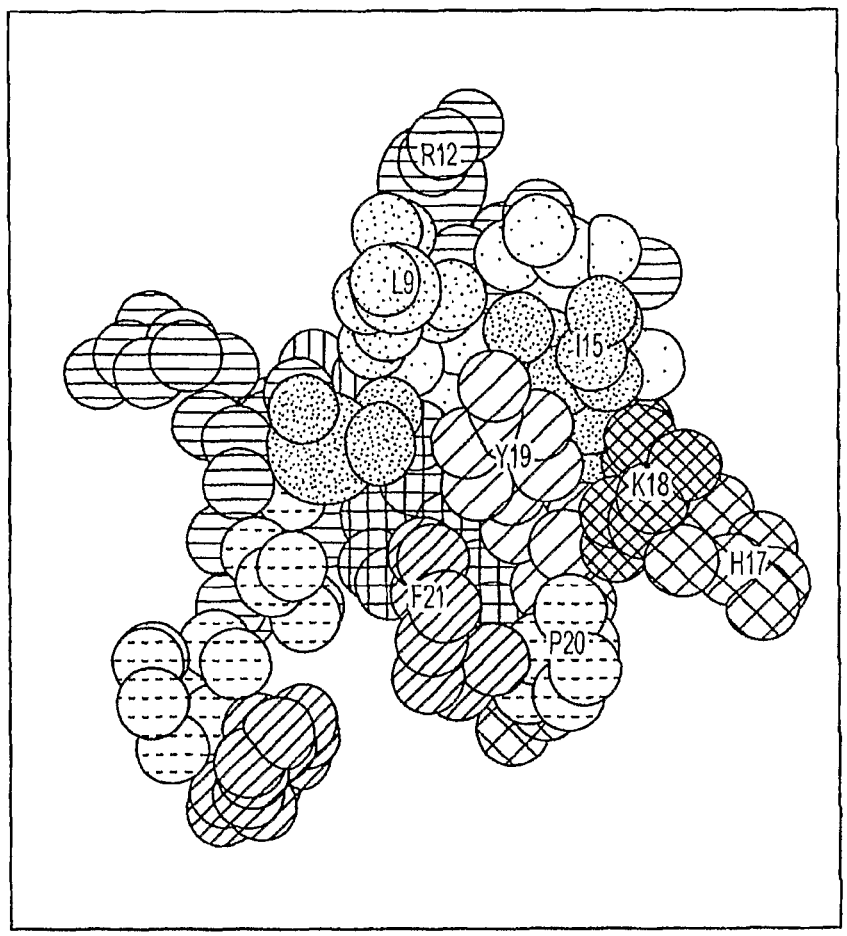

FIG. 18 shows the solution structure of p114a showing the relative roles of residues on enhancement of activity of p114a on the α3β4 subtype of rat neuronal nAChR. The structure is rendered in RasMol spacefill format and Shapely colors. The residues that gave greater enhancement of activity with alanine substitution are labeled in yellow and those that gave lesser enhancement of activity are labeled in white.

Figure 19:
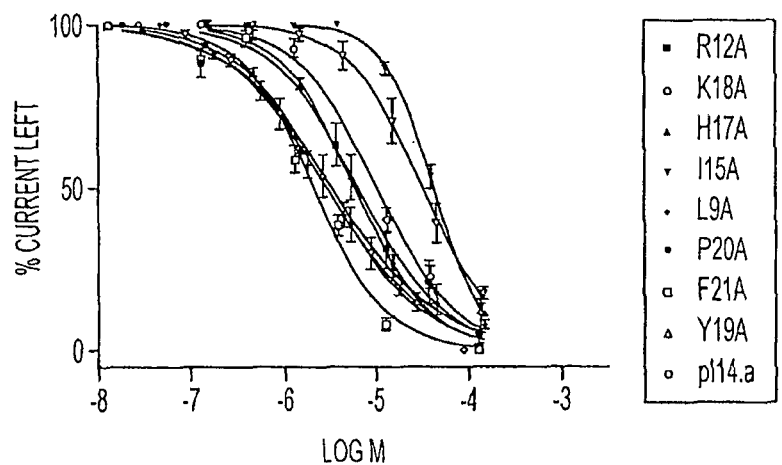

FIG. 19 shows the dose-response plots for p114a and alanine analogs on Kv1.6 channel.

Figure 20:
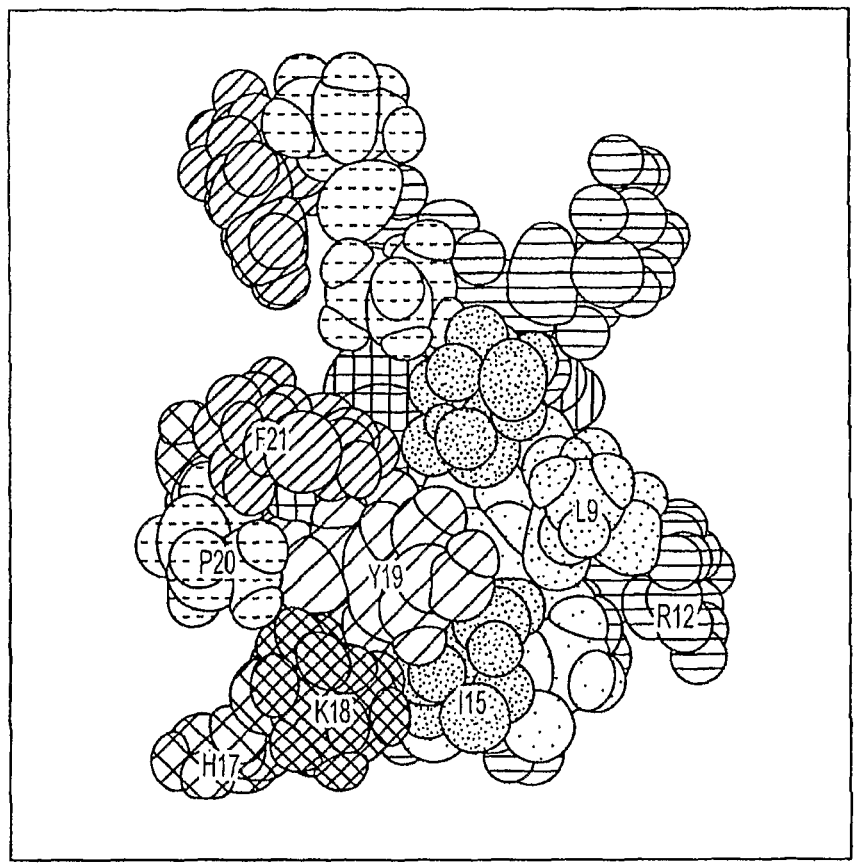

FIG. 20 shows the solution structure of p114a showing the relative roles of residues on activity of p114a on the Kv1.6 channel. The structure is rendered in RasMol spacefill format and Shapely colors. The residues that lowered the activity of p114a with alanine substitution are labeled in green or yellow, and those that slightly enhanced the activity with alanine substitution are labeled in white.

DETAILED DESCRIPTION OF THE INVENTION

The invention relates to relatively short peptides (termed J-Superfamily conotoxin peptides, J-conotoxins or J-conotoxin peptides herein), about 25 residues in length, which are naturally available in minute amounts in the venom of the cone snails or analogous to the naturally available peptides, and which preferably include two disulfide bonds. The J-conotoxins are useful for treating disorders involving voltage gated ion channels and/or receptors.

The present invention is further directed to cDNA clones encoding the precursor of the biologically-active mature peptides and to the precursor peptides.

The present invention, in another aspect, relates to a pharmaceutical composition comprising an effective amount of a J-superfamily conopeptide, a mutein thereof, an analog thereof, an active fragment thereof or pharmaceutically acceptable salts or solvates. Such a pharmaceutical composition has the capability of acting at voltage-gated ion channels, ligand-gated ion channels and/or receptors, and are thus useful for treating a disorder or disease of a living animal body, including a human, which disorder or disease is responsive to the partial or complete blockade of such channels or receptors comprising the step of administering to such a living animal body, including a human, in need thereof a therapeutically effective amount of a pharmaceutical composition of the present invention. The J-conotoxins are active at the voltage-gated potassium channel and some subtypes of the nicotinic acetylcholine receptor (nAChR).

For example, attention has been focused on the potassium channel, particularly its involvement in normal cellular homeostasis and its possible association with and derangements relating to a variety of disease states and immune responses. Considerable research has been expended and is currently underway in order not only to devise a treatment or prophylaxis against such devastating diseases, but also to study the underlying etiology(ies) such that a better understanding can be gained as to common denominators, if any, that would more directly focus a plan of attack for conquering them. Diseases having a particular association with such channels include autoimmune diseases and other proliferative disorders such as cancers. Autoimmune diseases include rheumatoid arthritis, type-1 diabetes mellitus (insulin dependent), multiple sclerosis, myasthenia gravis, systematic lupus erythematosus, Sjogren's syndrome, mixed connective tissue disease, experimental allergic encephalomyelitis (EAE), to name a few.

Potassium channels comprise a large and diverse group of proteins that, through maintenance of the cellular membrane potential, are fundamental in normal biological function. These channels are vital in controlling the resting membrane potential in excitable cells and can be broadly sub-divided into three classes: voltage-gated $K^+$ channels, $Ca^{2+}$ activated $K^+$ channels and ATP-sensitive $K^+$ channels. Many disorders are associated with abnormal flow of potassium ions through these channels. These disorders include multiple sclerosis, other demyelinating diseases (such as acute dissenmiated encephalomyelitis, optic neuromyelitis, adrenoleukodystrophy, acute transverse myelitis, progressive multifocal leukoencephalopathy), sub-acute sclerosing panencephalomyelitis (SSPE), metachromatic leukodystrophy, Pelizaeus-Merzbacher disease, spinal cord injury, botulinum toxin poisoning, Huntington's chorea, compression and entrapment neuropathies (such as carpal tunnel syndrome, ulnar nerve palsy), cardiovascular disorders (such as cardiac arrhythmias, congestive heart failure), reactive gliosis, hyperglycemia, immunosuppression, cocaine addiction, cancer, cognitive dysfunction, disorders resulting from defects in neurotransmitter release (such as Eaton-Lambert syndrome), and reversal of the actions of curare and other neuromuscular blocking drugs. Other uses of compounds that are active at $K^+$ channels are described in U.S. Published Patent Application No. 2002/0102607 A1, U.S. Published Patent Application No. 2004/0092447 A1, U.S. Published Patent Application No. 2005/0137132 A1 and U.S. Published Patent Application No. 2006/0014673 A1, each incorporated herein by reference.

There are two main classes of nAChRs: 1) the neuronal type; and 2) the muscle type. Neuronal type nAChRs are present both pre- and post-synaptically in the central and peripheral nervous systems, while the muscle type nAChRs are found post-synaptically at skeletal neuromuscular junctions (Wonnacott, 1997). The main difference between these receptors is their subunit composition. The neuronal type receptors are formed from the combination of α and β subunits or α subunits alone, while the muscle type receptors are composed of α, β, γ and ε (or δ) subunits. The functional receptors have different combinations of subunits (see Karlin, 2002), and have a range of pharmacological properties (see Albuquerque et al., 1997; Lukas et al., 1999 for review). Compounds, including conotoxins, with specificity for neuromuscular junction nAChRs are useful as neuromuscular blocking agents for use in conjunction with surgery. Compounds, including conotoxins, with specificity for neuronal nAChRs are useful for treating disorders regulated at neuronal nAChRs receptors. Such disorders include, but are not limited to, cardiovascular disorders, gastric motility disorders, urinary incontinence, nicotine addiction, mood disorders (such as bipolar disorder, unipolar depression, dysthymia and seasonal effective disorder) and small cell lung carcinoma, as well as the localization of small cell lung carcinoma. The neuronal nAChR has been implicated in the pathophysiology of Alzheimer's disease (Guan et al., 2000), Parkinson's disease (Aubert et al., 1992), schizophrenia (Mukherjee et al., 1994), small cell lung carcinoma (Codignola et al., 1996) nicotine addiction (U.S. Pat. No. 5,780,433, U.S. Pat. No. 5,866,682), pain (Marubio et al., 1999), and as neuromuscular blocking agents, such as muscle relaxants (U.S. Pat. No. 6,268,473 and U.S. Pat. No. 6,277,825) and in certain forms of epilepsy (Steinlein et al., 1995).

The invention is further directed to the use of these peptides for screening drugs for activity at the receptor of these conopeptides and to isolate and assay receptors.

The conopeptides of the present invention are identified by isolation from *Conus* venom. Alternatively, the conopeptides of the present invention are identified using recombinant DNA techniques by screening cDNA libraries of various *Conus* species using conventional techniques such as the use of reverse-transcriptase polymerase chain reaction (RT-PCR) or the use of degenerate probes. Primers for RT-PCR are based on conserved sequences in the signal sequence and 3' untranslated region of the J-superfamily conopeptide genes. Clones which hybridize to these probes are analyzed to identify those which meet minimal size requirements, i.e., clones having approximately 300 nucleotides (for a precursor peptide), as determined using PCR primers which flank the cDNA cloning sites for the specific cDNA library being examined. These minimal-sized clones are then sequenced. The sequences are then examined for the presence of a peptide having the characteristics noted above for conopeptides. The biological activity of the peptides identified by this method is tested as described herein, in U.S. Pat. No. 5,635,347 or conventionally in the art.

These peptides are sufficiently small to be chemically synthesized. General chemical syntheses for preparing the foregoing conopeptides are described hereinafter, along with specific chemical synthesis of conopeptides and indications of biological activities of these synthetic products. Various ones of these conopeptides can also be obtained by isolation and purification from specific *Conus* species using the techniques described in U.S. Pat. No. 4,447,356 (Olivera et al., 1984), U.S. Pat. No. 5,514,774 (Olivera et al., 1996) and U.S. Pat. No. 5,591,821 (Olivera et al., 1997), the disclosures of which are incorporated herein by reference.

The conopeptides can also be produced by recombinant DNA techniques well known in the art. Such techniques are described by Sambrook et al. (1989). The peptides produced in this manner are isolated, reduced if necessary, and oxidized to form the correct disulfide bonds, if present in the final molecule.

One method of forming disulfide bonds in the conopeptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conopeptide molecule. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropyl-carbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing g-carboxyglutamic acid residues is exemplified by Rivier et al. (1987), Nishiuchi et al. (1993) and Zhou et al. (1996). Synthesis of conopeptides have been described in U.S. Pat. No. 4,447,356 (Olivera et al., 1984), U.S. Pat. No. 5,514,774 (Olivera et al., 1996) and U.S. Pat. No. 5,591,821 (Olivera et al., 1997).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$- resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder and Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder and Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1987).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above. A suitable method for cyclization is the method described by Cartier et al. (1996).

Muteins, analogs or active fragments, of the foregoing J-superfamily of conopeptides are also contemplated here: See, e.g., Hammerland et al. (1992). Derivative muteins, analogs or active fragments of the conotoxin peptides may be synthesized according to known techniques, including conservative amino acid substitutions, such as outlined in U.S. Pat. No. 5,545,723 (see particularly col. 2, line 50 to col. 3, line 8); U.S. Pat. No. 5,534,615 (see particularly col. 19, line 45 to col. 22, line 33); and U.S. Pat. No. 5,364,769 (see particularly col. 4, line 55 to col. 7, line 26), each incorporated herein by reference.

Pharmaceutical compositions containing a compound of the present invention as the active ingredient can be prepared according to conventional pharmaceutical compounding techniques. See, for example, *Remington: The Science and Practice of Pharmacy,* 21st Ed., Lippincott Williams & Wilkins, Philadelphia, 2005. Typically, an antagonistic amount of active ingredient will be admixed with a pharmaceutically acceptable carrier. The carrier may take a wide variety of forms depending on the form of preparation desired for administration, e.g., intravenous, oral, parenteral or intrathecally. For examples of delivery methods see U.S. Pat. No. 5,844,077, incorporated herein by reference.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:

(a) pump (see, e.g., Luer and Hatton (1993), Zimm et al. (1984) and Ettinger et al. (1978));

(b) microencapsulation (see, e.g., U.S. Pat. Nos. 4,352,883; 4,353,888; and 5,084,350);

(c) continuous release polymer implants (see, e.g., U.S. Pat. No. 4,883,666);

(d) macroencapsulation (see, e.g., U.S. Pat. Nos. 5,284,761, 5,158,881, 4,976,859 and 4,968,733 and published PCT patent applications WO92/19195, WO 95/05452);

(e) naked or unencapsulated cell grafts to the CNS (see, e.g., U.S. Pat. Nos. 5,082,670 and 5,618,531);

(f) injection, either subcutaneously, intravenously, intra-arterially, intramuscularly, or to other suitable site; or (g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

The active agent is preferably administered in an therapeutically effective amount. By a "therapeutically effective amount" or simply "effective amount" of an active compound is meant a sufficient amount of the compound to treat the desired condition at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or spealists, and typically takes account of the disorder to be treated, the condition of the individual patient, the site of delivery, the method of administration and other factors known to practitioners. Examples of techniques and protocols can be found in *Remington: The Science and Practice of Pharmacy.*

Dosage may be adjusted appropriately to achieve desired drug levels, locally or systemically. Typically the active agents of the present invention exhibit their effect at a dosage range from about 0.001 mg/kg to about 250 mg/kg, preferably from about 0.01 mg/kg to about 100 mg/kg of the active ingredient, more preferably from a bout 0.05 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example, 24 hours or multiple doses per day are contemplated to achieve appropriate systemic levels of compounds.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The pharmaceutical compositions will generally contain from about 0.0001 to 99 wt. %, preferably about 0.001 to 50 wt. %, more preferably about 0.01 to 10 wt. % of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines and therapeutic agents in all of the major areas of clinical medicine. When used with other pharmaceutically active compounds, the conopeptides of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination with a supplementary potentiating agent. The individual drugs of the cocktail are each administered in therapeutically effective amounts. A therapeutically effective amount will be determined by the parameters described above; but, in any event, is that amount which establishes a level of the drugs in the area of body where the drugs are required for a period of time which is effective in attaining the desired effects.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., *Molecular Cloning* (Cold Spring Harbor Laboratory Press, Cold Spring Harbor, N.Y., 1982); Sambrook et al., *Molecular Cloning,* 2nd Ed. (Cold Spring Harbor Laboratory Press, Cold Spring Harbor, N.Y., 1989); Sambrook and Russell, *Molecular Cloning,* 3rd Ed. (Cold Spring Harbor Laboratory Press, Cold Spring Harbor, N.Y., 2001); Ausubel et al., *Current Protocols in Molecular Biology* (John Wiley & Sons, updated through 2005); Glover, *DNA Cloning* (IRL Press, Oxford, 1985); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, *Antibodies*, (Cold Spring Harbor Laboratory Press, Cold Spring Harbor, N.Y., 1998); Jakoby and Pastan, 1979; *Nucleic Acid Hybridization* (B. D. Harries & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology,* 6th Edition, (Blackwell Scientific Publications, Oxford, 1988); Hogan et al., *Manipulating the Mouse Embryo*, (Cold Spring Harbor Laboratory Press, Cold Spring Harbor, N.Y., 1986); Westerfield, M., *The zebrafish book A guide for the laboratory use of zebrafish* (*Danio rerio*), 4th Ed., (Univ. of Oregon Press, Eugene, Oreg., 2000).

EXAMPLES

The present invention can be described by reference to the following Examples, which are offered by way of illustration and are not intended to limit the invention in any manner. Standard techniques well known in the art or the techniques specifically described below were utilized.

Example 1

Material and Methods

Isolation of pl14a from *C. planorbis* Venom.

*Conus planorbis* is commonly found in the Indo-Pacific region and belongs to Clade IX in the phylogenetic scheme for *Conus* of Espiritu et al. (2001), equivalent to E5 of Duda et al. (2001). Snails were collected in the Marinduque Islands, Philippines, and dissected. Venom was pressed out of the venom ducts, and the venom pooled from several snails was lyophilized and stored at −70° C. A 500 mg portion was resuspended in 35 mL of 30% acetonitrile and 0.2% trifluoroacetic acid (TFA) using a vortex mixer for 2×1 min with an interval of 5 min on ice. The mixture was sonicated using a Branson LS-75 probe for 3×0.5 min on ice with 1 min rest periods, and the sediment was pelleted in a Beckman Avanti centrifuge with an F650 rotor for 30 min at 37500 g. The supernatant was diluted with 0.1% TFA, centrifuged again to remove all residual particles, and applied to a preparative Vydac C18 high-pressure liquid chromatography (HPLC) column (2.5 cm×25 cm). Venom peptides were eluted from the column with a linear gradient from 4.5 to 90% acetonitrile with 0.1% TFA at 0.9% acetonitrile/min. The flow rate was 20 mL/min, and the absorbance of the eluate was monitored at 220 nm. An analytical Vydac C18 HPLC column (4.6 mm×250 mm) with linear gradients at 0.18 or 0.09% acetonitrile/min in 0.1% TFA was used for subsequent fractionations. The flow rate was 1 mL/min, and absorbance at 220 and 280 nm was monitored.

pl14a Synthesis.

Linear pl14a was assembled on a Boc-phe-pam resin as previously described in Alewood (1997). A Boc-amide linker and Boc-amino acids were preactivated with an equivalent amount of 2-(1H-benzotriazol-1-yl)-1,1,3,3-tetramethyluronium hexafluoro-phosphate in the presence of diisopropylethylamine. Each coupling was monitored by the ninhydrin reaction except coupling to proline, which was monitored by the isatin test. HF cleavage was carried out at 5° C. for 1.5 h.

The crude linear peptide was purified by HPLC on a semi-preparative C18 column (1 cm×25 cm) with an elution gradient of 0.9% acetonitrile/min in 0.1% TFA. Folding was achieved by air oxidation at a peptide concentration of 0.1-0.2 mM in 0.1 M ammonium bicarbonate (pH 8) for 20 h. Coelution with native pl14a was demonstrated using an analytical C18 HPLC column with a linear gradient of 0.45 or 0.18% acetonitrile/min in 0.1% TFA. The flow rate was 1 mL/min in a Waters Millennium HPLC system with auto sampler.

Characterization of Peptides.

Mass determinations on both native and synthetic peptides were accomplished by matrixassisted laser desorption ionization (MALDI), or electrospray ionization (ESI) mass spectrometry (MS) at the University of Utah Mass Spectrometry and Proteomic Core Facility, the Salk Institute Peptide Biology Lab, and The University of Queensland Institute for Molecular Bioscience. The amidation of the C-terminus was shown on the native peptide from mass values obtained by ESI-MS.

The disulfide bond connectivity was determined using the partial reduction and alkylation procedure as described previously in Gray (1993). Partial reduction was achieved in the presence of 10 mM tris(2-carboxyethyl)phosphine hydrochloride (TCEP-HCl) in 0.085 M sodium citrate, 0.05% TFA, and 14% acetonitrile (pH 3) for 20 min at 23° C. The products were separated by HPLC, and the putative reduced peaks were alkylated using iodoacetamide. The alkylation reaction mixtures were fractionated by HPLC, and the partially alkylated product was identified by mass spectrometry. Alkylation after complete reduction with 10 mM dithiothreitol was done using 0.7% 4-vinylpyridine. The sequences of partially and fully alkylated peptides were determined by R. Schackmann, using Edman degradation chemistry in an Applied Biosystems model 477A protein sequencer at the Protein/DNA Core Facility of the University of Utah Huntsman Cancer Institute.

NMR Spectroscopy and Structure Calculations.

Samples for 1H NMR measurements contained ~1 mM peptide in a 95% H2O/5% D2O mixture (v/v) at pH ~3. Spectra were recorded at 290 K on a Bruker Avance-600 spectrometer equipped with a shielded gradient unit. Two-dimensional NMR spectra were recorded in phase-sensitive mode using time-proportional phase incrementation for quadrature detection in the $t_1$ dimension as previously described for other disulfide-rich peptides (Daly et al., 2004 and Rosengren et al., 2003). $^3J_{HN-H\alpha}$ coupling constants were measured from a one-dimensional spectrum or from the DQF-COSY spectrum.

Spectra were processed on a Silicon Graphics Indigo workstation using XWINNMR (Bruker) software. The $t_1$ dimension was zero-filled to 1024 real, data points, and 90° phase-shifted sine bell window functions were applied prior to Fourier transformation. Chemical shifts were referenced to internal 2,2-dimethyl-2-silapentane-5-sulfonate.

Preliminary structures of pl14a were calculated using a torsion angle simulated annealing protocol within DYANA (Guntert, et al., 1997). Final structures were calculated using CNS version 1.1 (Brunger et al., 1997). A set of 50 structures was generated by a torsion angle simulated annealing protocol as previously described (Daly et al., 2004 and Rosengren et al. 2003). Structures were analyzed using PROMOTIF (Hutchinson and Thornton, 1996) and PROCHECK-NMR (Laskowski et al., 1996).

Cloning.

Total RNA preparations from a single duct each of *C. planorbis* and *Conus ferrugineus* were obtained using the Qiagen RNeasy mini protocol for isolation of total RNA from animal tissues. Each RNA preparation (4.5 μg for *C. planorbis* and 5.1 μg for *C. ferrugineus*) was used in cDNA synthesis (Frohman, 1990). The 3'-untranslated region (UTR) for pl14a was identified by synthesizing degenerate oligonucleotide primers designed from the carboxy-terminal regions of the peptide, and the primers were used in a 3'-rapid amplification of cDNA ends (RACE) (Frohman, 1990). Another oligonucleotide primer was designed from the identified 3'-UTR and used in a 5'-RACE using the Clonetech SMART RACE kit and protocol.

Oligonucleotide primers derived from the 3"-UTR and 5'-prepropeptide regions of the pl14a clone were used to screen the cDNAs described above for more clones in the J superfamily. All PCR runs were done in a Peltier Thermal Cycler 2000 instrument using Invitrogen High Fidelity Platinum Taq DNA polymerase. The Invitrogen TA cloning kit was used for all transformations. DNA sequencing was carried out at the University of Utah Huntsman Cancer Institute Protein/DNA Core Facility using samples prepared following the Qiagen mini prep kit protocol.

The sequences of all oligonucleotide primers derived from the native peptide or clones are as follows:

3'RACE $1^{st}$ amplification: $Q_O$ (Frohman, 1990) and Primer 033 (derived from pl14a sequence . . . GIGHKYP . . . ) (SEQ ID NO:16)

Primer 033: GGNATHGGNCAYAAATATC (SEQ ID NO:17)

$2^{nd}$ amplification: $Q_1$ (Frohman, 1990) and Primer 031 (derived from pl14a sequence . . . HKYPFCHC . . . ) (SEQ ID NO:18)

Primer 031: CAYAARTAYCCNTTYTGYCAYTG (SEQ ID NO:19)

5' RACE $1^{st}$ amplification: SMART RACE universal primer and Primer 041 (derived from the 3'UTR) with the sequence: GCGTCATTGGAATGAGTATGCCGTC (SEQ ID NO:20)

2nd amplification: SMART RACE nested primer and Primer 042 (derived from the 3'UTR and upstream of Primer 041): CCGCGTCCCGTTTCCCTCTGCAATG (SEQ ID NO:21)

J-superfamily Screening Primers

Primer 041 (above) and Primer 045 (derived from the sequence obtained in the 5' RACE)

Primer 045: CCATGCCGTCTGTTCGGTCTGTG (SEQ ID NO:22)

Biological Assays.

Intracranial injections were administered to mice that were 15-17 days old. Peptide samples were resuspended in 12 μL of normal saline solution and administered to the mice using an insulin syringe. The peptide-injected mice were observed side by side with saline injected controls continuously for 2-4 h and checked the next day.

nAChR Assay.

Recordings were made from *Xenopus* oocytes expressing mouse skeletal muscle nAChR subtypes and rat neuronal subtypes, in a static bath of ND-96 solution as previously described in Cartier et al. (1996). Oocytes were injected 1-2 days after harvesting and used for voltage clamp recording 3-8 days after injection. The bath contained bovine serum albumin at a concentration of 0.1 mg/mL to minimize non-specific adsorption of the toxin and atropine at 1 μM to block endogenous muscarinic acetylcholine receptors. Acetylcholine (ACh)-gated currents were elicited with 1-10 μM ACh for oocytes expressing the muscle skeletal subtypes and 100 μM ACh for oocytes expressing the neuronal subtypes. The toxin was allowed to equilibrate in the static bath for 5 min prior to pulsing with ACh by gravity perfusion.

Three oocytes were used for each data point. Dose response curves were fit to the equation % response+100/[1+(toxin concentration/IC50)nH], where nH is the Hill coefficient.

K+ Channel Assays.

The *Xenopus* oocyte expression system was used to study the effect of pl14a on Kv1 channels. Oocytes were treated, and Kv1 channels were expressed as described previously in Jacobsen et al. (2000). Whole-cell currents were recorded under two-electrode voltage-clamp control using a Turbo-Tec amplifier (npi electronic, Tamm, Germany). Current records were low-pass-filtered at 1 kHz (−3 db) and sampled at 4 kHz. The bath solution was normal frog Ringer's solution (Horton et al., 1993) containing 115 mM NaCl, 2.5 mM KCl, 1.8 mM CaCl2, and 10 mM Hepes (pH 7.2) (NaOH). All electrophysiological experiments were performed at room temperature (19-22° C.).

The $IC_{50}$ values for the block of the Kv1.6 channel were calculated from the peak currents at a test potential of 0 mV according to the equation $IC_{50}$) fc/(1−fc)×[Tx], where fc is the fractional current and [Tx] is the toxin concentration. Tests on *Xenopus* oocytes expressing Kv2.1 and Kv3.4 channels were done under similar conditions.

Other Activity Assays.

The activity of pl14a was also tested in *Xenopus* oocytes xpressing the Nav1.2 channel, under conditions similar to those used in the K+ channel assays. The effect of pl14a on the binding of [$^{125}$I]GVIA to rat synaptosomes was tested using the membrane filtration assay (Cruz et al., 1987).

Example 2

Isolation and Structural Characterization of pl14a

An initial fractionation of *C. planorbis* venom was carried out to isolate and characterize major venom components. To identify conotoxin-like components, major components within the 2-4 kDa range were completely reduced and alkylated. The number of disulfide bonds in specific peptides within the mass range given above was obtained by mass spectrometry of samples before and after complete reduction and alkylation.

The chromatograms in FIG. 1 show the HPLC separation of the venom components of *C. planorbis* and the isolation of pl14a. The complete reduction and alkylation of the peak indicated in FIG. 1C suggested the presence of four cysteines. However, the MALDI and ESI average mass of 2911 Da for this conopeptide was approximately double the mass of peptides in known conotoxin superfamilies (A and T) with a four-cysteine pattern (Terlau and Olivera, 2004). Sequencing showed that the peptide has a cysteine pattern different from those in the previously characterized four-cysteine superfamilies (FIG. 2). The ESI monoisotopic mass value of 2909.5 Da for the native peptide indicated an amidated C-terminus. This peptide is initially called pl14a, based on the species name (*C. planorbis*) followed by the number representing the $14^{th}$ cysteine pattern found in conotoxins (Moller et al., 2005), with the letter "a" representing the first peptide characterized in this class from *C. planorbis*. As we will demonstrate below, the peptide defines a new superfamily of conotoxins, which we call the J-conotoxin superfamily.

Example 3

Peptide Synthesis and Determination of Disulfide Connectivity pl14a was chemically synthesized as described in Materials and Methods. Panels A-C of FIG. 3 show the HPLC chromatograms of the sample isolated from the venom, the predominant form obtained after overnight air oxidation at pH 8, and the coelution of both, respectively, which indicates that the folded synthetic preparation of pl14a is identical to the peptide present in the venom. A yield of 0.45 mg of pl14a was typically obtained from 1 mg of linear peptide.

Panels A and B of FIG. 4 show the HPLC profiles of the partial reduction and alkylation reactions, respectively. The partially reduced pl14a overlaps with the native folded peptide but can be completely separated from it after partial alkylation using the iodoacetamide reagent (Gray, 1993). Sequencing of both the partially alkylated peptide and of the peptide with pyridylethylation of the second pair of cysteines showed a 1-3, 2-4 disulfide connectivity (FIG. 2).

Example 4

Solution Structure of pl14a

NMR spectral assignments for pl14a were made using established techniques (Wutrich, 1986); the $^1$H chemical shifts are shown in Table 2. The chemical shifts in the amide region are well-dispersed, and the large number of resolved cross-peaks in the NOESY spectrum allowed determination of a well-defined structure for the majority of the molecule.

TABLE 2

| 1H Chemical Shifts of Conotoxin pl14a | | | | |
|---|---|---|---|---|
| 4 | 4.561 | 0.000 | HA | 1 |
| 6 | 3.295 | 0.000 | HB2 | 1 |
| 7 | 3.062 | 0.000 | HB3 | 1 |
| 21 | 7.329 | 0.001 | QD | 1 |

TABLE 2-continued

1H Chemical Shifts of Conotoxin pl14a

| | | | | |
|---|---|---|---|---|
| 27 | 4.487 | 0.006 | HA | 2 |
| 29 | 2.293 | 0.006 | HB2 | 2 |
| 30 | 1.869 | 0.002 | HB3 | 2 |
| 35 | 1.994 | 0.006 | QG | 2 |
| 36 | 3.773 | 0.001 | HD2 | 2 |
| 37 | 3.444 | 0.005 | HD3 | 2 |
| 41 | 8.579 | 0.001 | HN | 3 |
| 43 | 4.608 | 0.004 | HA | 3 |
| 45 | 1.824 | 0.005 | HB2 | 3 |
| 46 | 1.760 | 0.004 | HB3 | 3 |
| 51 | 1.681 | 0.002 | QG | 3 |
| 55 | 3.185 | 0.000 | QD | 3 |
| 69 | 4.400 | 0.004 | HA | 4 |
| 73 | 2.402 | 0.006 | QB | 4 |
| 77 | 1.998 | 0.008 | QG | 4 |
| 78 | 3.986 | 0.002 | HD2 | 4 |
| 79 | 3.654 | 0.002 | HD3 | 4 |
| 83 | 8.652 | 0.001 | HN | 5 |
| 85 | 4.090 | 0.000 | HA | 5 |
| 87 | 1.861 | 0.000 | HB2 | 5 |
| 88 | 1.725 | 0.001 | HB3 | 5 |
| 93 | 1.640 | 0.001 | QG | 5 |
| 109 | 8.290 | 0.001 | HN | 6 |
| 111 | 4.083 | 0.002 | HA | 6 |
| 113 | 1.859 | 0.007 | HB | 6 |
| 114 | 0.722 | 0.003 | QG2 | 6 |
| 120 | 1.135 | 0.002 | HG12 | 6 |
| 123 | 0.759 | 0.001 | QD1 | 6 |
| 130 | 7.960 | 0.001 | HN | 7 |
| 132 | 4.462 | 0.005 | HA | 7 |
| 134 | 3.099 | 0.005 | HB2 | 7 |
| 135 | 2.840 | 0.004 | HB3 | 7 |
| 140 | 8.161 | 0.003 | HN | 8 |
| 142 | 4.361 | 0.003 | HA | 8 |
| 144 | 2.878 | 0.008 | HB2 | 8 |
| 145 | 2.827 | 0.004 | HB3 | 8 |
| 149 | 7.720 | 0.001 | HD21 | 8 |
| 154 | 7.660 | 0.000 | HN | 9 |
| 156 | 4.162 | 0.001 | HA | 9 |
| 160 | 1.730 | 0.003 | QB | 9 |
| 162 | 1.613 | 0.006 | HG | 9 |
| 163 | 0.890 | 0.004 | QD1 | 9 |
| 164 | 0.846 | 0.000 | QD2 | 9 |
| 176 | 8.384 | 0.002 | HN | 10 |
| 178 | 3.946 | 0.002 | HA | 10 |
| 179 | 1.217 | 0.004 | QB | 10 |
| 186 | 8.488 | 0.002 | HN | 11 |
| 188 | 4.557 | 0.004 | HA | 11 |
| 190 | 3.316 | 0.002 | HB2 | 11 |
| 191 | 2.957 | 0.004 | HB3 | 11 |
| 196 | 7.577 | 0.001 | HN | 12 |
| 198 | 4.198 | 0.003 | HA | 12 |
| 202 | 1.924 | 0.002 | QB | 12 |
| 206 | 1.734 | 0.001 | QG | 12 |
| 222 | 7.887 | 0.003 | HN | 13 |
| 224 | 4.418 | 0.004 | HA | 13 |
| 225 | 1.491 | 0.006 | QB | 13 |
| 232 | 7.787 | 0.001 | HN | 14 |
| 234 | 4.182 | 0.001 | HA1 | 14 |
| 235 | 3.993 | 0.001 | HA2 | 14 |
| 239 | 7.862 | 0.002 | HN | 15 |
| 241 | 4.633 | 0.001 | HA | 15 |
| 243 | 2.145 | 0.001 | HB | 15 |
| 244 | 0.901 | 0.006 | QG2 | 15 |
| 250 | 1.441 | 0.004 | HG12 | 15 |
| 251 | 1.173 | 0.001 | HG13 | 15 |
| 253 | 0.957 | 0.004 | QD1 | 15 |
| 260 | 8.632 | 0.002 | HN | 16 |
| 262 | 3.912 | 0.000 | HA1 | 16 |
| 263 | 3.492 | 0.003 | HA2 | 16 |
| 267 | 8.631 | 0.003 | HN | 17 |
| 269 | 4.326 | 0.003 | HA | 17 |
| 273 | 3.149 | 0.005 | QB | 17 |
| 284 | 7.690 | 0.002 | HN | 18 |
| 286 | 3.905 | 0.005 | HA | 18 |
| 288 | 1.523 | 0.005 | HB2 | 18 |
| 289 | 1.395 | 0.005 | HB3 | 18 |
| 294 | 0.927 | 0.000 | QG | 18 |
| 298 | 1.080 | 0.000 | QD | 18 |
| 302 | 2.880 | 0.000 | QE | 18 |
| 306 | 7.584 | 0.000 | QZ | 18 |
| 309 | 7.413 | 0.003 | HN | 19 |
| 311 | 4.553 | 0.002 | HA | 19 |
| 315 | 2.245 | 0.007 | QB | 19 |
| 328 | 6.726 | 0.001 | QE | 19 |
| 329 | 6.955 | 0.002 | QD | 19 |
| 334 | 4.191 | 0.002 | HA | 20 |
| 336 | 2.282 | 0.005 | HB2 | 20 |
| 337 | 1.967 | 0.006 | HB3 | 20 |
| 342 | 2.030 | 0.005 | QG | 20 |
| 343 | 3.636 | 0.003 | HD2 | 20 |
| 344 | 3.426 | 0.006 | HD3 | 20 |
| 348 | 6.754 | 0.002 | HN | 21 |
| 350 | 4.397 | 0.003 | HA | 21 |
| 352 | 3.261 | 0.122 | HB2 | 21 |
| 353 | 3.173 | 0.122 | HB3 | 21 |
| 367 | 7.152 | 0.001 | QD | 21 |
| 368 | 7.377 | 0.003 | QE | 21 |
| 371 | 7.741 | 0.003 | HN | 22 |
| 373 | 4.692 | 0.004 | HA | 22 |
| 375 | 2.947 | 0.005 | HB2 | 22 |
| 376 | 2.845 | 0.009 | HB3 | 22 |
| 381 | 8.143 | 0.003 | HN | 23 |
| 383 | 4.391 | 0.000 | HA | 23 |
| 387 | 3.254 | 0.002 | QB | 23 |
| 398 | 8.676 | 0.000 | HN | 24 |
| 400 | 4.672 | 0.004 | HA | 24 |
| 402 | 3.181 | 0.004 | HB2 | 24 |
| 403 | 2.874 | 0.001 | HB3 | 24 |
| 408 | 8.772 | 0.001 | HN | 25 |
| 410 | 4.241 | 0.000 | HA | 25 |
| 412 | 1.837 | 0.000 | HB2 | 25 |
| 413 | 1.772 | 0.000 | HB3 | 25 |
| 416 | 1.680 | 0.000 | HG2 | 25 |
| 417 | 1.629 | 0.000 | HG3 | 25 |
| 422 | 3.173 | 0.002 | QD | 25 |

The three-dimensional structure of pl14a was calculated with 178 distance restraints and 19 angle restraints using a simulated annealing protocol in CNS. Ten restraints for five hydrogen bonds were included, based on the slowly exchanging amide protons and preliminary structures. The resulting family of structures had good structural and energetic statistics, as shown in Table 3. An ensemble and ribbon representation of the three-dimensional structure is shown in FIG. 5. Analysis of the structures with PROMOTIF in Hutchinson and Thornton (1996) identified an α-helical region between residues 6 and 12 and 310-helices between residues 15-17 and 20-22.

TABLE 3

NMR and Refinement statistics for pl14A

| | |
|---|---|
| NMR distance and dihedral constraints | |
| distance constraints | |
| total NOE | 178 |
| sequence ($|i - j| = 1$) | 93 |
| medium-range ($|i - j| < 5$) | 54 |
| long-range ($|i - j| > 5$) | 31 |
| total dihedral angle restraints | |
| ø | 15 |
| χ$_1$ | 4 |
| structures statistics | |
| violations (mean ± standard deviation) | |
| distance constraints (Å) | 0.035 ± 0.003 |
| dihedral angle constraints (deg) | 0.025 ± 0.2 |

TABLE 3-continued

NMR and Refinement statistics for pl14A

| maximum dihedral angle violations (deg) | 3 |
| maximum distance constraint violations (Å) | 0.3 |
| deviations from idealized geometry | |
| bond lengths (Å) | 0.003 ± 0.0002 |
| bond angles (deg) | 0.46 ± 0.02 |
| impropers (deg) | 0.31 ± 0.02 |
| average pairwise rmsd$^a$ (Å) | |
| heavy atoms (residues 7-23) | 0.16 ± 0.06 |
| backbone atoms (residues 7-23) | 1.50 ± 0.26 |
| Ramachandran statistics (residues 3-24) | |
| most favored | 80.6% |
| additionally allowed | 19.4% |

$^a$The pairwise and rmsd was calculated among 20 refined structures

Example 5

Pl14a Clone

The combined nucleotide sequence obtained for pl14a from both the 3' and 5' RACE experiments is set forth in SEQ ID NO:37 and the amino acid sequence of the encoded precursor peptide is set forth in SEQ ID NO:38. FIG. 6A shows the precursor sequence of pl14a. The only post-translational processing occurring in this peptide, which is C-terminal amidation, is demonstrated by the sequence . . . RGKR (SEQ ID NO:23) at cleavage site 3 in FIG. 6A (Eipper et al., 1991) which results in the amidation of the C-terminal R of the mature peptide. The unique signal sequence, MPSVRSVTC-CCLLWMMFSVQLVTP (SEQ ID NO:24), indicates that pl4a is the first peptide in a new superfamily of conotoxins that we have termed the J-superfamily. Using oligonucleotide primers from the signal sequence and the 3'-UTR, additional members of the J-superfamily were identified (FIG. 6B) from C. planorbis and C. ferrugineus, a species that also belongs to Clade IX. The peptide length, the loop sizes, and the C-terminal amidation are maintained among the peptides identified, so far. Residues R12, G16, H17, Y19, and P20 are conserved, and there is a conservative substitution of valine for 16. The nucleotide sequences encoding these members of the J-superfamily are set forth in SEQ ID NO:39 (pl14.1), SEQ ID NO:41 (pl14.2), SEQ ID NO:43 (pl14.3), SEQ ID NO:45 (fe14.1) and SEQ ID NO:47 (fe14.2). The propeptide sequences for these members of the J-superfamily are set forth in SEQ ID NO:40 (pl14.1), SEQ ID NO:42 (pl14.2), SEQ ID NO:44 (pl14.3), SEQ ID NO:46 (fe14.1) and SEQ ID NO:48 (fe14.2).

Example 6

Biological Activity of pl14a in Mice

Behavioral symptoms were elicited upon intracranial injection of the synthetic peptide in mice, indicating that this targets the mammalian central nervous system. At an average dose of 0.5 nmol/g of mouse body weight, the symptoms included rapid circling and shaking, with the shaking occurring when the mouse moved or attempted to move. These symptoms started as early as a few minutes after injection and lasted for an average of one to a few hours. At double the dose, the rapid circling and/or shaking symptoms were still observed in most cases, but more severe symptoms such as barrel rolling and seizures were common. Further doubling the dose resulted in death in at least 50% of the injected mice. Intraperitoneal injections at levels similar to those used in intracranial injections did not produce any apparent symptom in the mice.

Intramuscular injection in goldfish and injection at the anterior end of a marine polychaete (Nereis virens), likewise, did not give any definitive symptomatology.

Example 7

Activity in Nicotinic Acetylcholine Receptor Assays

Figure 7A:
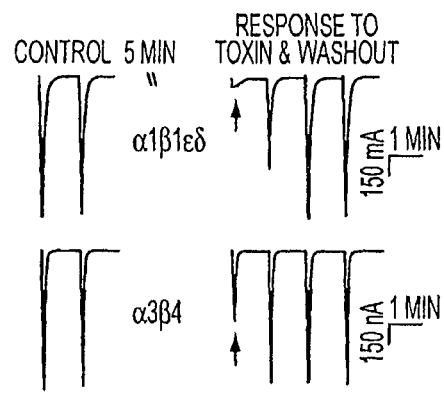
Figure 7B:
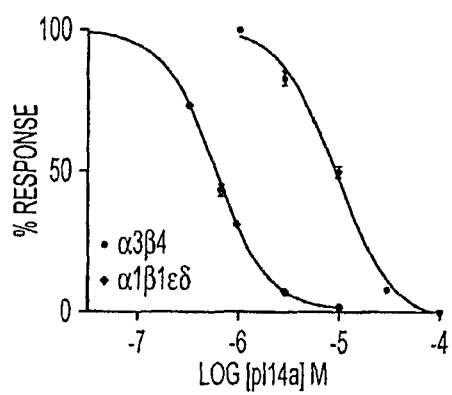
Figure 10:
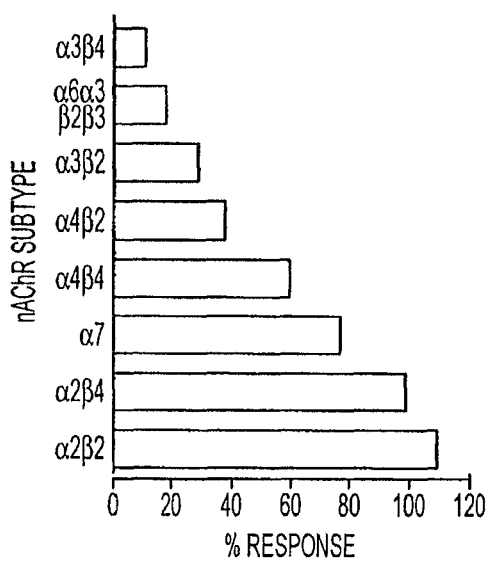

The synthetic pl14a was tested for activity in neuronal and muscle subtypes of nAChR expressed in oocytes. Initial tests were carried out at 10 μM, and in the muscle subtypes of the nAChR, the peptide was approximately 50% more active in the adult mouse subtype (α1β1εδ) than in the fetal form (α1β1γδ). The dose-response plot of the pl14a activity in α1β1εδ (FIG. 7) gave an $IC_{50}$ of 0.54 M. FIG. 7 also shows the dose-response plot of the activity in the α3β4 subtype of the rat neuronal nAChR, which gave the highest activity among eight neuronal forms that were tested (FIG. 10), and the $IC_{50}$ obtained was 8.7 μM.

Example 8

Activity in $K^+$ Channel Assays

Figure 8:
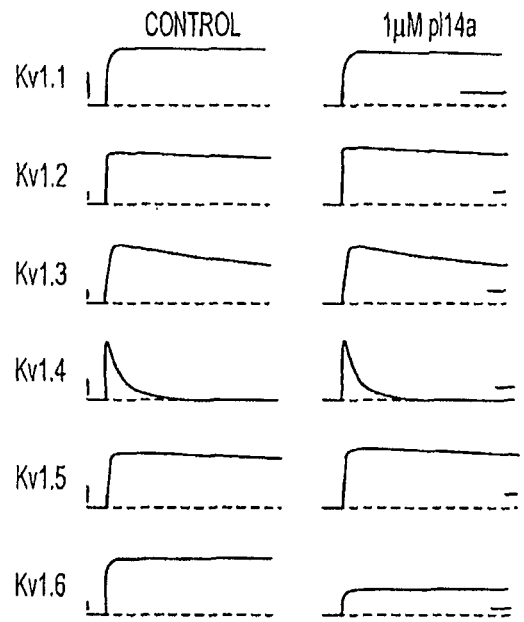

To investigate a potential interaction of pl14a with voltage-activated K+ channels, different isoforms in the Kv1 subfamily (Kv1.1-Kv1.6) were expressed in Xenopus oocytes, and potential changes for the evoked currents in the presence of 1 μM pl14a were measured. At this concentration, a very small blocking effect was observed for Kv1.1, and no effect was observed for Kv1.2-Kv1.5 (see FIG. 8). In contrast, a profound block of the currents was observed for Kv1.6. The $IC_{50}$ for the block was 1.59±0.96 μM (mean±the standard deviation; n=8). pl14a was also assayed in Xenopus oocytes expressing Kv2.1 and Kv3.4 channels. No inhibition of the evoked response was observed in these channels at 2 μM pl14a (data not shown).

Example 9

Other Activity Assays

The addition of 2 μM pl14a to Xenopus oocytes expressing the Nav1.2 channel also showed no effect on the evoked response, showing that pl14a does not affect these Na currents. The presence of 5 μM pl14a in an ö-GVIA membrane binding assay (Cruz et al., 1987) did not displace any binding of [125I]GVIA to rat synaptosomes (data not shown). This result implies that pl14a does not bind to N-type presynaptic Ca2+ channels.

We isolated and characterized a conotoxin from the Indo-Pacific worm-hunting cone C. planorbis, designated pl14a, which is 25 amino acid residue's long with a X6CX3CX10 CXCX cysteine pattern (FIG. 2). The only post-translational modification present in the peptide is amidation of the C-terminus, which was detected from the monoisotopic ESI mass value and confirmed by the presence of a standard amidation sequence at the C-terminal end of the precursor peptide ( . . . CGKR→ . . . C-NH2) (SEQ ID NO:25) (FIG. 6A) (Eipper et al., 1991). The disulfide connectivity was determined by stepwise reduction and alkylation and confirmed by the NMR solution structure (FIG. 5) to be C1-C3 and C2-C4, as shown in FIG. 2.

The cloning data provided evidence that the peptide we characterized from *C. planorbis* venom, conotoxin pl14a, belongs to a new gene superfamily, the J-conotoxin superfamily. Five homologous peptides (FIG. 6B) were identified in the cDNA prepared from the venom ducts of *C. planorbis* and the closely related species *C. ferrugineus*, using oligonucleotide primers derived from the signal sequence and the 3'-UTR of the p14a clone (FIG. 6A). It is notable that the peptides identified from these vermivorous species are identical in length and loop sizes to pl14a, and all are C-terminally amidated. However, unlike most conopeptides, the complete precursor sequence for most of the peptides in this superfamily has nine additional amino acid residues after the standard amidation sequence at the C-terminus of each mature peptide; these excised C-terminal sequences are highly conserved.

A recent report of a series of peptides from worm-hunting Western Atlantic cone species (Moller et al., 2005) showed that peptides with a C-C-C-C cysteine pattern may be common components of venoms of vermivorous cones. Furthermore, the loop sizes could be variable, as well as the disulfide connectivity. Table 3 compares all known peptide sequences with the 14$^{th}$ cysteine pattern that have been reported to date. The peptide from the venom of the piscivorous species *Conus geographus* (Olivera et al., 1990) shows that this cysteine pattern is also present in the venoms of piscivorous species. The question of whether all of the peptides in Table 4 belong to the J-superfamily remains. The screening of cDNA derived from other *Conus* species for J-superfamily peptides is ongoing.

The three-dimensional structure of pl14a (FIG. 5) represents a novel structural fold and is well-defined, with the exception of the N-terminal region. This disorder is likely to be from structural flexibility, as there are no disulfide bonds in the N-terminal region to constrain the molecule. The major element of secondary structure is an α-helix between residues 6 and 12. Both disulfide bonds (7-22 and 11-24) have one half-cystine located in this helical region, and formation of the disulfide bonds results in a compact three-dimensional structure. Although the disulfide connectivity of pl14a is the same as that of the α-conotoxins (i.e., C1-C3, C2-C4), the secondary structure and the position of the C-terminus are not conserved. Despite these differences, there are structural similarities between the backbone conformation for residues 11-21 in pl14a and the conformation observed for residues 4-12 in α-conotoxin SI. As the α-conotoxins are antagonists of the nAChR and possess a common structural motif, the similarities between pl14a and α-conotoxin SI may be relevant to the activity of pl14a observed at the nAChR.

A novel characteristic of the biological activity of pl14a is its effect on the activities of both voltage-gated and ligand-gated ion channels. The activity of pl14a on nAChR subtypes could be attributed to structural similarities with α-conotoxins. Table 5 shows an alignment of the sequence of pl14a with those of some α-conotoxins. The lower IC$_{50}$ observed for pl14a on the adult muscle nAChR subtype over the neuronal ones is consistent with the degree of sequence similarity between pl14a and the α-conotoxins, which are known to be potent blockers of the muscle subtype, being greater than that

TABLE 4

Conotoxins with the 14$^{th}$ Cysteine Framework (C-C-C-C)

| Name | Primary Structure (SEQ ID NO:) | Disulfude Connectivity | Snail species | Reference |
| --- | --- | --- | --- | --- |
| pl14a | FPRPRICNLACRAGIGHKYPFCHCR* (10) | C1-C3, C2-C4 | *C. planorbis* | this work |
| pl14.1 | GPGSAICNMACRLGQGHMYPFCNCN* (11) | — | *C. planorbis* | this work |
| pl14.2 | GPGSAICNMACRLEHGHLYPFCHCR* (12) | — | *C. planorbis* | this work |
| pl14.3 | GPGSAICNN1ACRLEHGHLY PFCNCD* (13) | — | *C. planorbis* | this work |
| fe14.1 | SPGSTICKMACRTGNGHKYPFCNCR* (14) | — | *C. ferrugineus* | this work |
| fe14.2 | SSGSTVCKMMCRLGYGHLYPSCGCR* (15) | — | *C. ferrugineus* | this work |
| — | KFLSGGFYγIVCHRYCAKGIAKEFCNCPD* (26) | — | *C. geographus* | Olivera et al., 1990 |
| flf14a | WDVNDCIHFCLIGVVERSYTECHTMCT* (27) | C1-C4, C2-C3 | *C. floridanus floridensis* | Moller et al., 2005 |
| flf14b | WDVNDCIHFCLIGVVGRSYTECHTMCT* (28) | C1-C4, C2-C3 | *C. floridanus floridensis* | Moller et al., 2005 |
| flf14c | WDAYDCIQFCMRPEMRHTYAQCLSICT* (29) | C1-C4, C2-C3 | *C. floridanus floridensis* | Moller et al., 2005 |
| vil14a | GGLGRCIYNCMNSGGGLSFIQCKTMCY* (30) | C1-C4, C2-C3 | *C. villepinii* | Moller et al., 2005 |

*An amidated C-terminus.

The dominant symptomatology observed in mice intracranially injected with pl14a was the excitotoxic effect of the peptide on the central nervous system. The absence of symptoms with intraperitoneal injections in mice and intramuscular injections in fish implies that pl14a does not act directly on the peripheral nervous system.

shown with known blockers for the neuronal subtype α3β4. In a SAR study on the residues in α-GI and in α-SI that are critical to the binding to nAChRs in mouse muscle-derived BC$_3$H-1 cells and *Torpedo* (Groebe et al., 1997), it was shown that residues 9 and 10 were involved in the interaction of these conotoxins with the receptor. The corresponding residues in pl14a (residues 17 and 18, respectively) and the adjacent ones (highlighted residues) are closely related, if not identical, to those in the α-conotoxins. The fact that the potency of pl14a is much lower than that of GI or SI could be due to subtle changes in the secondary structure that is presented.

TABLE 5

Sequence Homologies Between pl14a and α-Conotoxin Blockers of nAChR

| Name | Primary Structure (SEQ ID NO:) | $IC_{50}$ in muscle subtype (nM) | $IC_{50}$ in α3β4 (nM) | Reference |
|---|---|---|---|---|
| α-MI | GRCCHPACGKNYSC-NH$_2$ (31) | 12.0 (α1β1γδ) | | Johnson et al., 1995 |
| α-GI | ECCNPACGRHYSC-NH$_2$ (32) | 20.0 (α1β1γδ) | | Johnson et al., 1995 |
| α-SI | ICCNPACGPKYSC-NH$_2$ (33) | 170 (α1β1γδ) | | Groebe et al., 1997 |
| pl14A | FPRPRICNLACRAGIGHKYPFCHCR-NH$_2$ (10) | 540 (α1β1εδ) | 8700 | this work |
| α-AuIB | GCCSYPPCFATNPDC-NH$_2$ (34) | | 750 | Luo et al., 1998 |
| α-PeIA | GCCSHPACSVNHPELC-NH$_2$ (35) | | 480 | McIntosh et al., 2005 |
| α-BuIA | GCCSTPPCAVLYC-NH$_2$ (36) | | 27.7 | Azam et al., 2005 |

Figure 9:
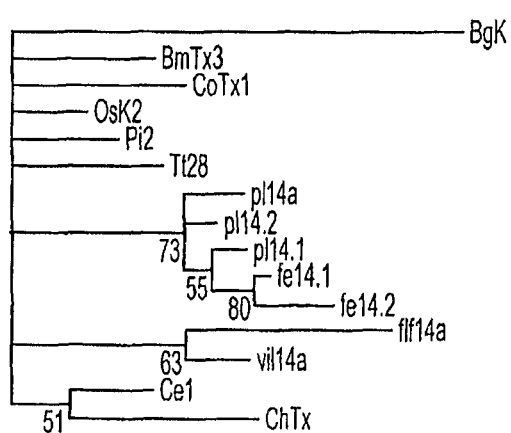

A number of diverse conotoxins were previously shown to affect other K$^+$ channels. These include the κ- (Shon et al., 1998) and κM-conotoxins in Ferber et al. (2003) and the conkunitzins (Bayruhuber et al., 2005; Imperial et al., 2006), all from fish-hunting *Conus* species. To our knowledge, this is the first report of a peptide that selectively inhibits the Kv1.6 channel activity among the different Kv1 forms. A very diverse group of peptides identified in animal toxins have been found to block Kv1 channel subtypes (Cotton et al., 1997, Fajloun et al., 2000; and Chagot et al., 2005). A phylogenetic tree was generated from some of these toxins and is shown in FIG. 9. The conotoxins form two different branches from the rest of the toxins from scorpion and sea anemone. All J-superfamily peptides are in one branch and separate from the other conotoxins with the same cysteine framework but with a different three-dimensional structure.

Figures 11A, 11B:
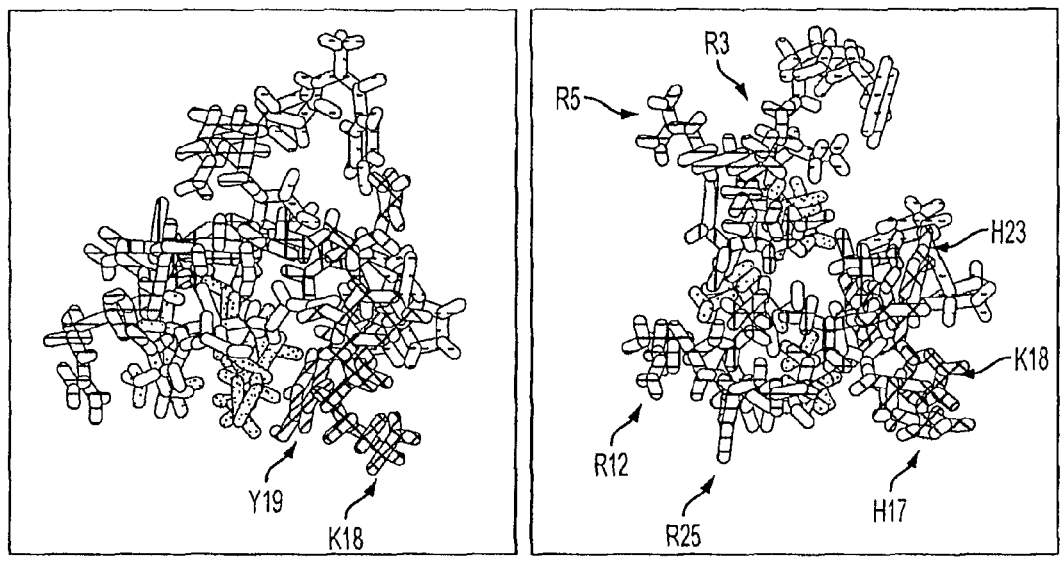

Two types of structural features are shared and have been proposed to play a role in the activity on Kv1 channels. The first is a diad structure, made up of a positively charged (usually lysine) and a hydrophobic amino acid (usually aromatic), protruding from a relatively flat surface made up of the other amino acid residues of the peptide. The lysine α-carbon and the center of the aromatic ring are within 6-7 Å of each other (Srinivasan et al., 2002 and Dauplais et. al., 1997), with the lysine residue occluding the K+ channel pore (Gilquin et al., 2002). In some Kv1 channel inhibitors without the functional dyad, the presence of a ring of basic residues on one surface of the molecule has been demonstrated to play a role in the binding of a peptide to the outer vestibule of the channel (Verdier et al., 2005 and Mouhat, et al., 2004). There is both a potential diad as well as a ring of basic residues in pl14a; one or both of these structural elements may be important for the interaction of the peptide with the Kv1.6 channel. See FIGS. 11A-11B.

The demonstration of the activity of pl14a on both the Kv1.6 channel and in nAChR subtypes is the first observation of a *Conus* peptide inhibiting both a voltage-gated and a ligand-gated ion channel. The symptomatology observed in mice treated with the peptide suggests that the K+ channel activity is the dominant effect in mammals in vivo.

The role of specific residues in pl14a that may affect either or both of these activities on the nAChR subtypes and Kv1.6 was examined by the chemical syntheses and functional evaluation of alanine-substituted analogs. The results of these SAR studies are presented in Example 10.

Example 10

SAR Studies on pl14a

A unique characteristic of pl14a is its ability to inhibit a voltage-gated ion channel, Kv1.6 and a group of ligand-gated ion channels, which include subtypes of the nAChR. As discussed above, there are similarities in the sequence and structure of pl14a with α-conotoxins, which could explain the nAChR antagonist activity. On the other hand, a potential diad or a ring of basic residues may play a role in K$^+$ channel inhibition.

An initial SAR experiment was conducted using truncated analogs of pl14a. The biological activity of each analog was evaluated by means of mouse bioassay and electrophysiological assay in *Xenopus* oocytes expressing Kv1.6 channel and nAChR subtypes.

Further SAR experiments utilizing analogs with single alanine substitutions were designed to evaluate the role of specific residues on the activity of pl14a in each of the three molecular targets that were studied above. These targets were the α1β1εδ muscle subtype and the α3β4 neuronal subtype of nAChR, and the Kv1.6 channel. The same set of alanine-substituted analogs was tested in each assay. A factor that was considered in the choice of residues that were substituted with alanine was the conservation of specific residues observed among homologous peptides that were identified in *C. planorbis* and *C. ferrugineus*. A few other residues that were either large or charged were also included in the study.

Figure 12:
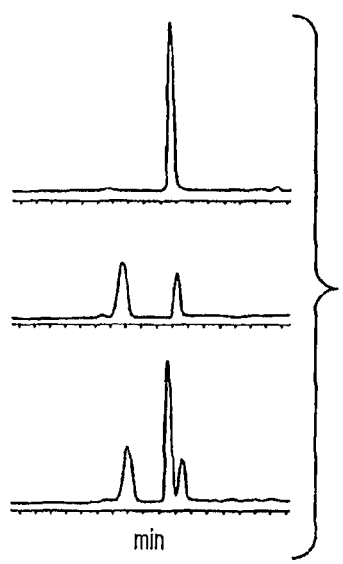

Syntheses of Truncated pl14a Analogs:

Truncated analogs TrA, TrB and TrC were assembled following the Boc procedure as described above. Folding was done through air oxidation in 0.1M ammonium bicarbonate pH 8 for 16 to 20 h at room temperature. One major oxidized form was obtained for pl14aTrA; pl14aTrB and pl14aTrC yielded two major forms each. An example of the HPLC profile of the oxidation reaction mixture of pl14aTrB is shown in FIG. 12. A similar profile was obtained for the oxidation reaction mixture of pl14aTrC.

```
pl14a     FPRPRICNLACRAGIGHKYPFCHCR (SEQ ID NO: 10)
pl14aTrA  FPRPRICNLACRAGIGHKYPFCHC  (SEQ ID NO: 49)
pl14aTrB        CNLACRAGIGHKYPFCHCR (SEQ ID NO: 50)
pl14aTrC        CNLACRAGIGHKYPFCHC  (SEQ ID NO: 51)
```

The oxidation reaction of the analogs without the six residues before the first cysteine, consistently gave two major oxidized peaks for both pl14aTrB and pl14aTrC. These results suggest that at least one of the six residues that were excluded in the syntheses of these truncated analogs was necessary for the folding of native pl14a into a single predominant form under the same oxidation conditions. It is noteworthy that among the native peptides identified from *C. planorbis* and *C. ferrugineus* by cDNA cloning, the residue right before the first cysteine, $I^6$, is conserved in five out of the six homologous sequences. The substitution in the sixth peptide is conservative ($I^6$ to $V^6$). The second residue $P^2$ is also conserved in five out of the six sequences, but the substitution in the sixth sequence is with an S residue. The results imply that the presence of isoleucine or valine close to the first cysteine in the peptide may have helped direct the oxidation to favor the formation of specific disulfide connectivities.

The three possible folding isomers of pl14a or the analogs have the following disulfide connectivities: 1: $C_1$-$C_3$, $C_2$-$C_4$; 2: $C_1$-$C_4$, $C_2$-$C_3$; 3: $C_1$-$C_2$, $C_3$-$C_4$. Native pl14a, which has the $C_1$-$C_3$, $C_2$-$C_4$ is very slightly more hydrophobic than the linear form and elutes right after the linear form in $C_{18}$ HPLC columns. The HPLC chromatogram of the oxidized pl14aTrB (FIG. 12) indicates that pl14aTrB folding isomer 2 (peak B), which elutes right after the linear form, most probably has the $C_1$-$C_3$, $C_2$-$C_4$ configuration that matches the disulfide connectivity of native pl14a.

Biological Activity of Truncated Analogs:

The results of intracranial injections in mice are tabulated in Table 6, and the results obtained from Kv1.6 assays done by A. Sporning (Terlau Lab, Max Planck) are summarized in Table 7. The mouse bioassay results implied that the truncations did not affect the activity elicited by pl14a with intracranial injection. On the other hand, the Kv1.6 results indicated a possible role of one or more residues in the N-terminal sequence before the first cysteine.

TABLE 6

Activity of pl14a and Truncated Analogs in Mice by Intracranial Injection

| | nmol per mouse 15-17 days old | Number of Injected* mice | Number of mice with symptoms | | |
|---|---|---|---|---|---|
| Peptide | | | Circling and/or Shaking** | Barrel-rolling and/or seizures | Death |
| pl14a | 4.6 | 2 | 2 | 2 | 0 |
| | 2.3 | 4 | 1 | 0 | 0 |
| pl14aTrA | 7.4 | 2 | 2 | 2 | 0 |
| | 3.7 | 4 | 3 | 0 | 0 |
| pl14aTrB | 4.5 | 3 | 3 | 3 | 1 |
| folding isomer 1 | 2.2 | 6 | 4 | 3 | 0 |

TABLE 6-continued

Activity of pl14a and Truncated Analogs in Mice by Intracranial Injection

| | nmol per mouse 15-17 days old | Number of Injected* mice | Number of mice with symptoms | | |
|---|---|---|---|---|---|
| Peptide | | | Circling and/or Shaking** | Barrel-rolling and/or seizures | Death |
| pl14aTrB folding isomer 2 | 3.3 | 3 | 2 | 3 | 2 |
| | 1.6 | 6 | 4 | 3 | 0 |
| pl14aTrC folding isomer 1 | 5.7 | 3 | 2 | 3 | 1 |
| | 2.8 | 6 | 4 | 2 | 1 |
| pl14aTrC folding isomer 2 | 5.8 | 3 | 3 | 3 | 0 |
| | 2.9 | 6 | 6 | 0 | 0 |

*6 NSS-injected control mice gave no symptoms.
**Shaking was more obvious when moving or attempting to move.

TABLE 7

Relative Activity of Truncated Analogs on Kv1.6 Channel Compared to pl14a

| Peptide | Concentration μM | Relative inhibition of Kv1.6 response |
|---|---|---|
| pl14a | 1 | +++ |
| pl14aTrA | 2 | ++ |
| pl14aTrB folding isomer 1 | 2 | --- |
| pl14aTrB folding isomer 2 | 2 | --- |
| pl14aTrC folding isomer 1 | 2 | --- |
| pl14aTrC folding isomer 2 | 2 | --- |

In an assay on the adult mouse muscle subtype of nAChR expressed in *Xenopus* oocytes, both isomers of pl14aTrB and pl14aTrC were as active as pl14a at 10 μM. The data suggests that unlike the activity on the Kv1.6 channel, the activity on the α1β1εδ muscle subtype of nAChR is independent of the presence the six N-terminal amino acid residues of pl14a.

The results of mice injections with the truncated analogs established the fact that the first six residues and the terminal residue of pl14a are not required in bringing about the symptoms typically observed with intracranial injections with pl14a. Furthermore, the results suggest that the type of disulfide connectivity is also not a factor in the production of symptoms in intracranially-injected mice. It is implied, therefore, that the critical residues that cause the production of symptoms following intracranial injection in mice are found within the sequence CNLACRAGIGHKYPFCHC (SEQ ID NO:51), and that this residue (or residues) is accessible in the two major folding isomers of pl14aTrB and pl14aTrC.

The apparent loss of activity on the Kv1.6 channel with truncation of six residues at the N-terminus (pl14aTrB and pl1aaTrC) indicates that at least one of the excluded residues is important for activity on this channel. The loss of the C-terminal R residue only slightly affected the activity of pl14aTrA on the same channel.

Syntheses of Alanine-substituted pl14a Analogs:

Crude linear samples were assembled and cleaved by P. S. Bansal (Alewood Lab, IMB University of Queensland). Peptide assembly was achieved with the Boc method and cleavage from the resin was accomplished using HF as described above.

Each of the linear peptide samples was purified by HPLC on a semi-prep C18 column using a gradient of 0.45% acetonitrile/min in 0.1% TFA for elution. Each purified linear peptide was lyophilized and oxidized following the method employed with pl14a, which involved air oxidation in 0.1 M ammonium bicarbonate pH 8 for 16 to 20 h.

Figure 13:
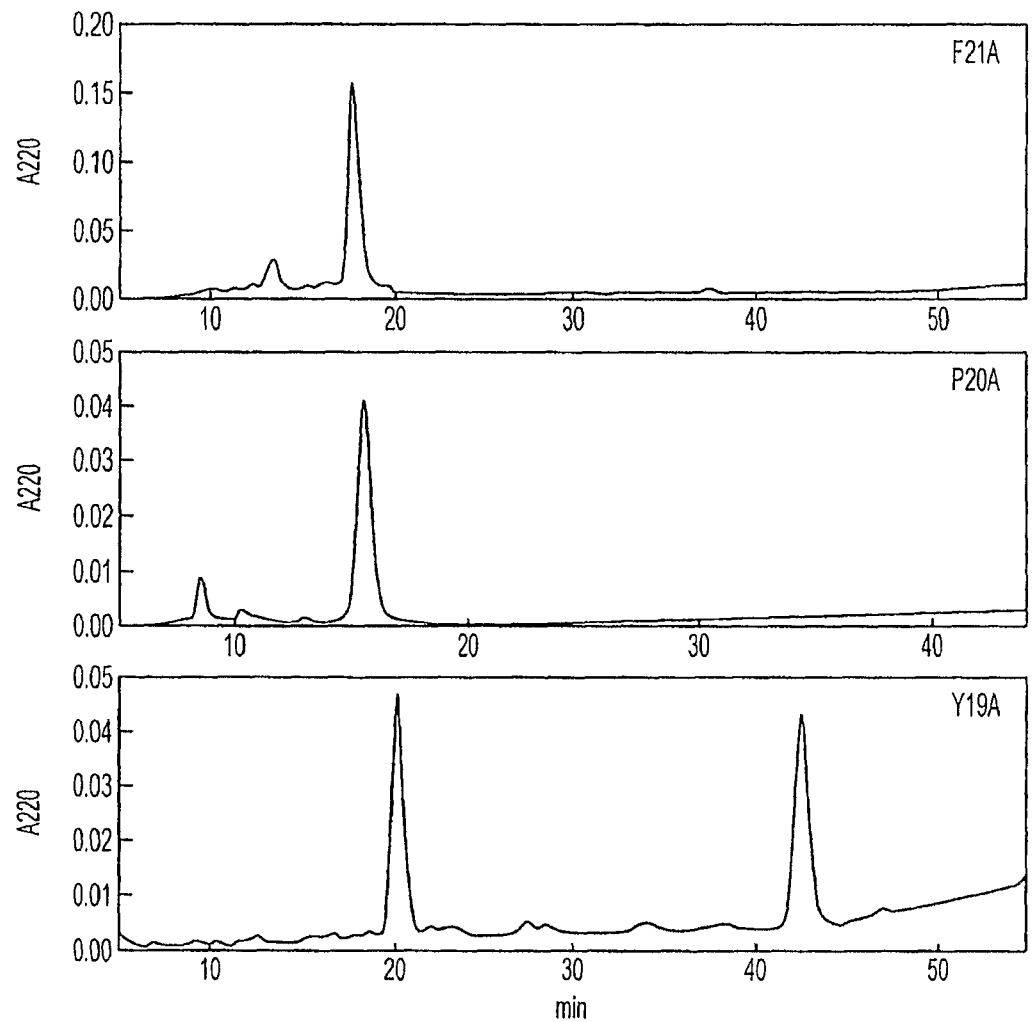
FIG. 13 shows the HPLC absorbance profiles of the oxidation reaction mixtures of some of the p114a alanine-substituted analogs at ~20 h. The elution gradient was 0.18% acetonitrile/min in 0.1% TFA.

The oxidation reactions were purified by HPLC in an analytical $C_{18}$ column, and slow gradients of ≤0.18% acetonitrile/min in 0.1% TFA were utilized to separate contaminating peaks close to the major oxidized form. FIG. 13 includes the HPLC absorbance profiles of oxidation reaction mixtures of some of the pl14a analogs. The Y19A analog yielded two major oxidized forms, unlike native pl14a and the other alanine-substituted analogs that produced one predominant oxidized form each under the same conditions. The short-ranged slow gradients used in the initial purification runs failed to detect the more hydrophobic oxidized form of the Y19A analog. This second folding isomer of pl14a[Y19A] has been purified for structure determination.

All analogs, except the more hydrophobic folding isomer of the Y19A analog, were assayed on mice and in *Xenopus* oocytes expressing each of the three molecular targets.

Characterization of the Disulfide Connectivities in the pl14a Analogs:

The set of secondary αH chemical shifts for each alanine-substituted analog was obtained and compared with the secondary shifts of pl14a by N. L. Daly (Craik Lab, IMB University of Queensland). This method allowed the verification of the secondary structure of each analog. The validity of SAR conclusions depends on whether or not the analogs retained the secondary structure of the native peptide. Each comparison is presented in FIG. 14. The less hydrophobic oxidized form of the Y19A analog is the only peptide that is indicated to have a disulfide connectivity that could be different from that of pl14a. The secondary shifts for the more hydrophobic oxidized form of pl14a[Y19A] are still to be measured.

The secondary αH chemical shifts for the alanine-substituted analogs, except for those of Y19A, established the secondary structures to be similar to that of native pl14a.

The oxidation reaction produced two major folding isomers for pl14a[Y19A]; the more hydrophobic form was not detected with the short and slow gradients used in the initial purification runs and was not included in the SAR experiments. The hydrophilic folding isomer of pl14a[Y19A], which was used in the experiments, was demonstrated to have a secondary structure different from that of native pl14a. Although the secondary shifts for pl14a[Y19A] were partly different from those of native pl14a, the possibility remains that the disulfide connectivity in pl14a [Y19A] is the same as that of native pl14a which is $C_1$-$C_3$, $C_2$-$C_4$.

Activity in Mouse Bioassays:

Each alanine-substituted analog elicited symptoms that were similar to those shown by pl14a in intracranially injected mice. These symptoms included splayed legs, shaking, circling, barrel-rolling, seizures and death. The data obtained from initial injections are presented in Tables 8 and 9. The values obtained for the ratio of the number of mice with symptoms to the number of mice injected with the analogs imply that none of the substitutions made a very drastic change on the effect of pl14a when administered in mice by intracranial injection.

TABLE 8

Symptomatology in Mice Injected with Native and Alanine-substituted pl14a

| Peptide | # of Mice with Symptomatology/# of Mice Injected | | |
|---|---|---|---|
| 5 to 10 nmol per mouse | Shaking/ Circling | Barrel-rolling Convulsion/seizure | Death |
| pl14A | 4/6 | 1/6 | 1/6 |
| pl14A[L9A] | 4/4 | 2/4 | 0/4 |
| pl14a[R12A] | 2/4 | 3/4 | 2/4 |
| pl14a[I15A] | 1/3 | 0/3 | 0/3 |
| pl14a[H17A] | 1/2 | 1/2 | 0/2 |
| pl14a[K18A] | 2/2 | 2/2 | 0/2 |
| pl14a[Y19A] | 1/2 | 1/2 | 0/2 |
| pl14a[P20A] | 2/2 | 1/2 | 0/2 |
| pl14a[F21A] | 1/3 | 1/3 | 0/3 |

TABLE 9

Symptomatology in Mice Injected with Native and Alanine-substituted pl14a

Figure 14:
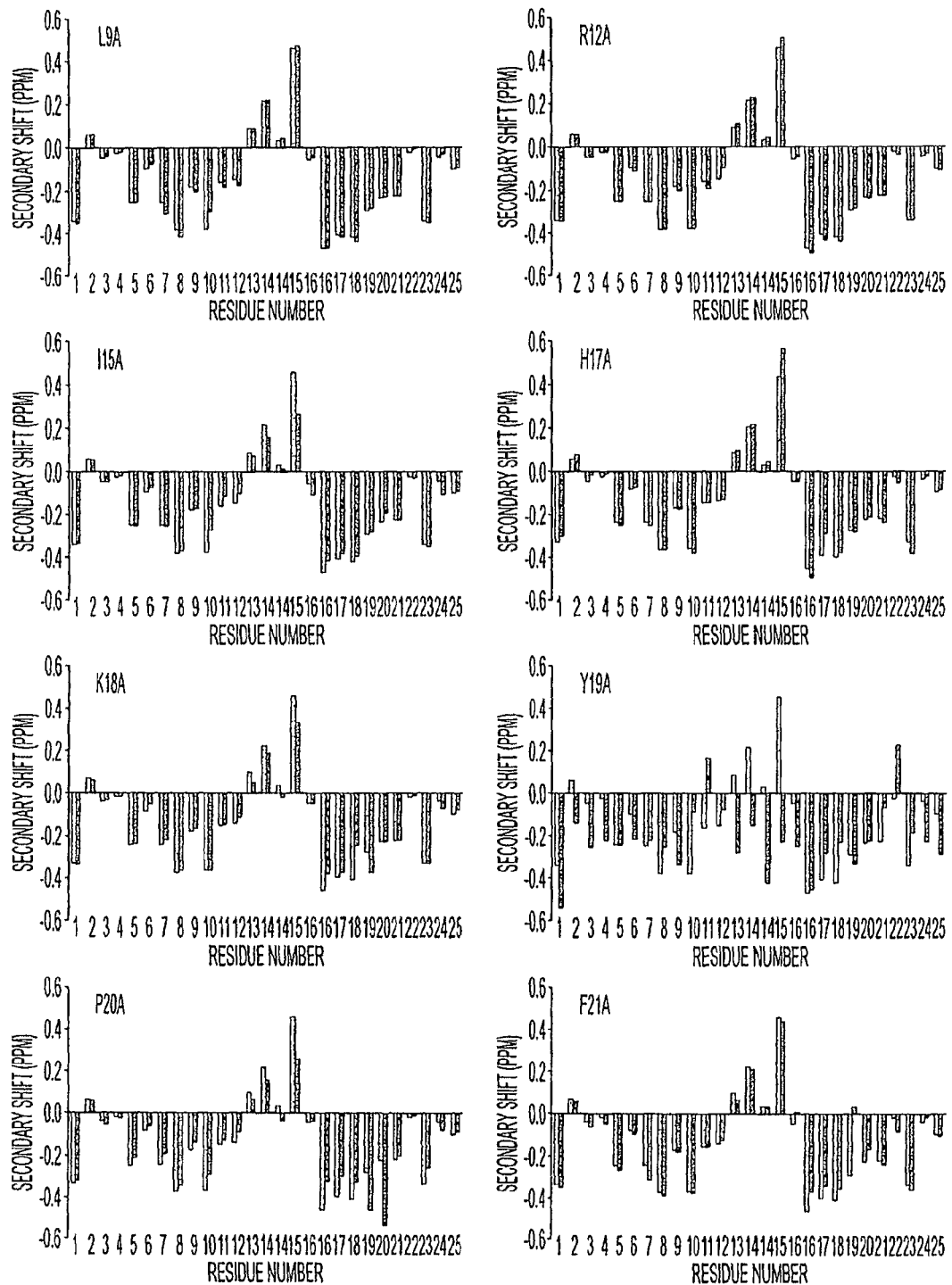
FIG. 14 shows the secondary αH chemical shifts of each alanine-substituted analog compared with those of p114a. The secondary shifts of p114a are colored red in each panel.
Figure 15:
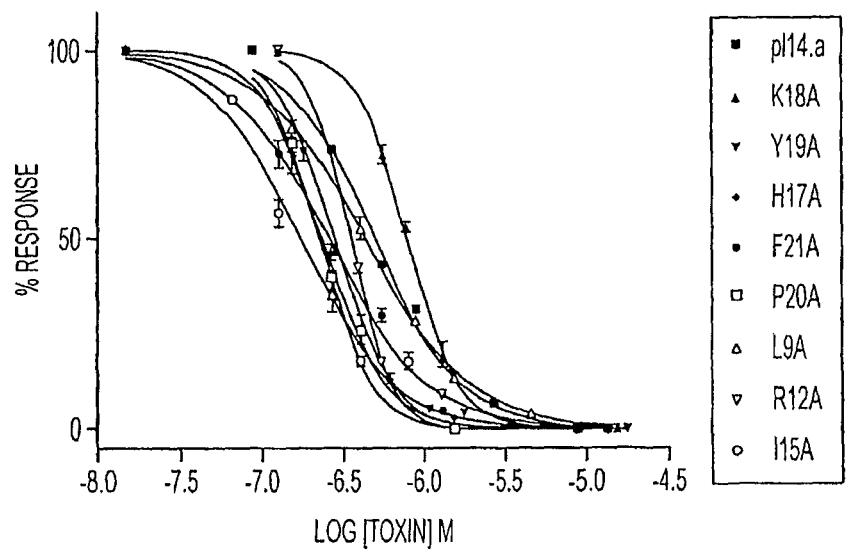
FIG. 15 shows dose-response plots for p114a and alanine analogs on α1β1εδ subtype of nAChR.

| Peptide | # of Mice with Symptomatology/# of Mice Injected | | |
|---|---|---|---|
| 15 nmol per mouse | Shaking/ Circling | Barrel-rolling Convulsion/seizure | Death |
| pl14A | 4/4 | 3/4 | 2/4 |
| pl14A[L9A] | 2/2 | 1/2 | 1/2 |
| pl14a[R12A] | 1/1 | 1/1 | 1/1 |
| pl14a[I15A] | 3/3 | 2/3 | 1/3 |
| pl14a[H17A] | 1/1 | 1/1 | 0/1 |
| pl14a[K18A] | 1/1 | 1/1 | 1/1 |
| pl14a[Y19A] | 0/1 | 1/1 | 1/1 |
| pl14a[P20A] | 1/1 | 0/1 | 1/1 |
| pl14a[F21A] | 0/1 | 1/1 | 1/1 | pl14a and the alanine-substituted analogs were assayed on *Xenopus* oocytes expressing the mouse α1β1εδ nAChR subtype by E. Lopez-Vera (Olivera Lab, University of Utah) as described above. FIG. 16 includes the plots of the alanine-substituted analogs of pl14a and native pl14a. The values for $IC_{50}$ obtained from the plots in FIG. 15 are listed in Table 10. The interpretation of the $IC_{50}$ value for the Y19A analog included in this experiment is considered unclear due to the difference in secondary structure with native pl14a (FIG. 14).

TABLE 10

$IC_{50}$ Values for pl14a and Alanine analogs on α1β1εδ Subtype of nAChR.

| Peptide | $IC_{50}$, nM | 95% Confidence Interval nM |
|---|---|---|
| pl14a[I15A] | 175 | 151-202 |
| pl14a[H17A] | 228 | 207-250 |
| pl14a[P20A] | 240 | 222-261 |
| pl14a[F21A] | 257 | 234-283 |
| pl14a[Y19A] | 285 | 246-331 |
| pl14a[R12A] | 355 | 330-382 |
| pl14a[L9A] | 434 | 409-461 |
| pl14a | 507 | 474-544 |
| pl14a[K18A] | 796 | 764-828 |

A slight but significant reduction of activity with substitution of alanine for $K^{18}$ in pl14a, as shown by the $IC_{50}$ value on the α1β1εδ subtype of mouse muscle nAChR, demonstrates that $K^{18}$ is necessary for the optimum activity of pl14a on the α1β1εδ subtype of mouse muscle nAChR. All the other alanine substitutions for bulkier residues caused slight enhancement of activity or reduction of $IC_{50}$ values, most probably due to a slight reduction in the steric hindrance to the availability of $K^{18}$ for interaction with the receptor site. As presented in FIG. XX, $L^9$, $R^{12}$, and $F^{21}$ are relatively distant from $K^{18}$ while $P^{20}$, $H^{17}$, and $I^{15}$ are adjacent to $K^{18}$. The relative distances of these residues from $K^{18}$ exhibit an inverse correlation with the magnitude of enhancement of pl14a activity. This observation supports the hypothesis on the reduction of steric hindrance with alanine substitution.

In an SAR study made on α-MI (Jacobsen et al., 1999), a Y12A substitution significantly reduced the affinity of the peptide to the mammalian α/δ interface in muscle nAChR. Other studies have demonstrated the importance of the $Y^{11}$ residue in α-GI for its activity on muscle nAChR (9). Since the secondary αH chemical shifts for the pl14a[Y19A] analog used in this study demonstrated a secondary structure that is different from that of native pl14a, the interpretation of results for Y19A in Table 10 is unclear.

Activity on α3β4 Subtype of Rat Neuronal nAChR:

pl14a and the analogs were assayed on *Xenopus* oocytes expressing the α3β4 subtype of nAChR by E. Lopez-Vera (Olivera Lab, University of Utah) as described above. FIG. 17 includes the plots of all the alanine-substituted analogs of pl14a and native pl14a. The values for $IC_{50}$ obtained from FIG. 18 are listed in Table 11. The interpretation of the $IC_{50}$ value for the Y19A analog is considered unclear at this stage due to the difference in secondary structure with native pl14a (FIG. 14).

TABLE 11

$IC_{50}$ Values for pl14a and Alanine Analogs on α3β4 Subtype of nAChR

| Peptide | $IC_{50}$ μM | 95% Confidence Interval |
|---|---|---|
| pl14a[P20A] | 0.71 | 0.65-0.78 |
| pl14a[L9A] | 1.36 | 1.18-1.56 |
| pl14a[I15A] | 1.60 | 1.36-1.90 |
| pl14a[F21A] | 2.85 | 2.42-3.35 |
| pl14a[R12A] | 3.21 | 2.52-4.08 |
| pl14a[H17A] | 3.92 | 3.28-4.69 |
| pl14a | 8.7 | 7.34-10.4 |
| pl14a[Y19A] | 10.36 | 9.62-11.15 |
| pl14a[K18A] | 11.48 | 10.14-13.00 |

No alanine substitution brought about a significant increase in the $IC_{50}$ of pl14a on the α3β4 subtype of rat neuronal nAChR other than a very slight increase with the substitution of $K^{18}$. A number of substitutions, however, brought about significant enhancement on the activity of pl14a on this nAChR subtype. The replacement of bulkier strongly hydrophobic groups ($L^9$ and $I^{15}$) with alanine enhanced the activity slightly more than the alanine substitution of the bulky charged groups ($R^{12}$ and $H^{17}$). The effect of alanine substitution of the weakly hydrophobic $F^{21}$ is closer to the effect of the bulky charged residues than to that of the strongly hydrophobic ones.

The highest level of enhancement obtained with the P20A analog could be due to its proximity to $K^{18}$ (FIG. 18) since the slight increase in the $IC_{50}$ of K18A implies that $K^{18}$ has a role in the interaction of pl14a with the α3β4 subtype of rat muscle nAChR. $P^{20}$ is also adjacent to $H^{23}$, which is located right behind $P^{20}$ in FIG. 18. It is of interest to examine the effect of alanine substitution of $H^{23}$ in future experiments, in addition to that of the pl14a[Y19A] isomer with the secondary structure closest to that of native pl14a.

Activity on Kv1.6 Channel:

pl14a and the analogs were assayed on *Xenopus* oocytes expressing the Kv1.6 channel by P. Chen (Olivera Lab, University of Utah) as described above. FIG. 19 includes the plots of all the alanine-substituted analogs of pl14a and native pl14a. The values for $IC_{50}$ obtained from the plots in FIG. 19 are listed in Table 12. The interpretation of the $IC_{50}$ value for the Y19A analog is considered unclear at this stage due to the difference in secondary structure with native pl14a (FIG. 14).

TABLE 12

$IC_{50}$ Values for pl14a and Alanine Analogs on Kv1.6 Channel

| Peptide | $IC_{50}$, μM | 95% Confidence Interval μM |
|---|---|---|
| pl14a[P20A] | 2.22 | 1.48-3.33 |
| pl14a[L9A] | 2.26 | 1.70-3.02 |
| pl14a[F21A] | 2.41 | 1.71-3.39 |
| pl14a | 3.12 | 2.53-3.85 |
| pl14a[H17A] | 4.60 | 3.11-6.80 |
| pl14a[R12A] | 6.54 | 4.04-10.62 |
| pl14a[K18A] | 7.88 | 5.38-11.55 |
| pl14a[Y19A] | 32.7 | 26.7-40.0 |
| pl14a[I15A] | 45.53 | 33.95-62 |

The difference in the value of the $IC_{50}$ for pl14a inhibition of Kv 1.6 response in this section and the $IC_{50}$ mentioned above is due to a difference in the oocytes used to express the channel. In the previous examples, the vitelline membrane was removed from each oocyte before clamping; the same membrane was retained in the oocytes used for the dose-response experiments in this example.

The $IC_{50}$ values listed in Table 12 demonstrate the major role of $I^{15}$ in the interaction of pl14a with the Kv1.6 channel. The highly significant effect of alanine substitution of the $Y^{19}$ residue cannot be attributed specifically to a role of $Y^{19}$ in the binding of pl14a to the channel since the secondary structure of the native peptide was not retained in the Y19A analog.

The minimal effect of the alanine substitution of $K^{18}$ on the activity suggests that the diad hypothesis does not apply to the pl14a-Kv1.6 channel interaction. Furthermore, the small changes in the $IC_{50}$ values with alanine substitution of $K^{18}$, $R^{12}$, and $H^{17}$ (FIG. 20) are insufficient to support the hypothesis of a ring of basic residues, which would include these three residues. However, there are four other basic residues ($R^3$, $R^5$, $H^{23}$, $R^{25}$) that were not included in this experiment, since these were not conserved among the homologous sequences obtained with cDNA cloning.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Abdel-Mottaleb, Y. et al. (2006). A novel toxin from the venom of the scorpion Tityus trivittatus is the first member of a new α-KTX subfamily. *FEBS Lett* 580:592-596.

Albuquerque, E. X. et al. (1997). Properties of neuronal nicotinic acetylcholine receptors: pharmacological characterization and modulation of synaptic function. *J Pharmacol Exp Ther* 280:1117-1136.

Alewood, P. F. et al. (1997) Rapid in situ neutralization protocols for Boc and Fmoc solid-phase chemistries. *Methods Enzymol* 289:14-29.

Aubert, I. et al. (1992). Comparative alterations of nicotinic and muscarinic sites in Alzheimer's and Parkinson's diseases. *J Neurochem* 58:529-541.

Azam, L. et al. (2005). κ-Conotoxin BuIA, a novel peptide from *Conus bullatus*. *J Biol Chem* 280:80-87.

Bayrhuber, M. et al. (2005). Conkunitzin-S1 is the first member of a new Kunitz-type neurotoxin family: Structural and functional characterization. *J Biol Chem* 180:21246-21255.

Bitan, G. et al. (1997). J Peptide Res 49:421-426.

Bodansky et al. (1966). Chem Ind 38:1597-98.

Brunger, A. T. et al. (1997). New applications of simulated annealing in X-ray crystallography and solution. *Structure* 5:325-336.

Cartier, G. E. et al. (1996). A new α-conotoxin which targets α3β2 nicotinic acetylcholine receptors. *J Biol Chem* 271:7522-7528.

Chagot, B. et al. (2005). An unusual fold for potassium channel blockers: NMR structure of three toxins from the scorpion Opisthacanthus madagascariensis. *Biochem J* 388:263-271.

Codignola, A. et al. (1996). alpha-Conotoxin imperialis I inhibits nicotine-evoked hormone release and cell proliferation in human neuroendocrine carcinoma cells. *Neurosci Lett* 206:53-56.

Cotton, J. et al. (1997). A potassium-channel toxin from the sea anemone Bundosoma granulifera, an inhibitor for Kv1 channels. Revision of the amino acid sequence, disulfide-bridge arrangement, chemical synthesis and biological activity. *Eur J Biochem* 244:192-202.

Cruz, L. J. et al. (1987). Characterization of the ω-conotoxin target. Evidence for tissue-specific heterogeneity in calcium channel types. *J Biol Chem* 26:820-824.

Daly, N. L. et al. (2004). Structures of μO-conotoxins from *Conus marmoreus*. Inhibitors of tetrodotoxin (TTX)-sensitive and TTX resistant sodium channels in mammalian sensory neurons. *J Biol Chem*. 279:25774-25782.

Dauplais, M. et al. (1997). On the convergent evolution of animal toxins. *J Biol Chem* 272:4302-4309.

Duda, T. F. et al. (2001). Origins of diverse feeding ecologies within *Conus*, a genus of venomous marine gastropods. *Biol J Linn Soc* 73:391-409.

Dudina, E. E. et al. (2001). OsK2, a new selective inhibitor of Kv1.2 potassium channels purified from the venom of the scorpion Orthochirus scrobiculosus. *Biochem Biophys Res Commun* 286:841-847.

Eipper, B. A. et al. (1991). Peptidyl-α-hydroxylglycine α-amidating lyase. *J Biol Chem* 266:7827-7833.

Espiritu, D. J. D. et al. (2001) Venomous cone snails: Molecular phylogeny and the generation of toxin diversity. *Toxicon* 39: 1899-1916.

Ettinger, L. J. et al. (1978). *Cancer* 41:1270-1273.

Fajloun, Z. et al. (2000). Chemical synthesis and characterization of Pi1, a scorpion toxin from Pandinus imperator active on K+ channels. *Eur J Biochem* 267:5149-5155.

Ferber, M. et al. (2003). A novel *Conus* peptide ligand for K+ channels. *J Biol Chem* 278:2177-2183.

Frohman, M. A. (1990). RACE: Rapid amplification of cDNA ends, in PCR Protocols (Innis, M. A., Ed.) pp. 28-45. Academic Press, San Diego.

Gilquin; B. et al. (2002). Structure of the BgKKv1.1 complex based on distance restraints identified by double mutant cycles. *J Biol Chem* 277:37406-37413.

Gray, W. R. (1993). Disulfide structures of highly bridged peptides: A new strategy for analysis. *Protein Sci.* 2:1732-1748.

Groebe, D. R. et al. (1997). Determinants involved in the affinity of α-conotoxins GI and SI for the muscle subtype of nicotinic acetylcholine receptors. *Biochemistry* 36:6469-6474.

Guan, Z. Z. et al. (2000). Decreased protein levels of nicotinic receptor subunits in the hippocampus and temporal cortex of patients with Alzheimer's disease. *J Neurochem* 74:237-243.

Guntert, P. et al. (1997). Torsion angle dyanmics for NMR structure calculation with the new program DYANA. *J Mol Biol* 273:283-298.

Hammerland, L. G. et al. (1992). *Eur J Pharmacol* 226:239-244.

Hargittai, B. et al. (2000). Chemical synthesis and biological activities of lactam analogues of alphs-contotoxin SI. *J Med Chem* 43:4787-4792.

Heading, C. (1999). *Curr Opin CPNS Invest Drugs* 1:153-166.

Horton, R. M. et al. (1993). The 'embryonic' γ subunit of the nicotinic acetylcholine receptor is expressed in adult extraocular muscle. *Neurology* 43, 983-986.

Houben-Weyl, *Methoden der Organischen Chemie (Houben-Weyl): Synthese von Peptiden*, E. Wunsch (Ed.), Georg Thieme Verlag, Stuttgart, Ger. (1974).

Hrubry, V. et al. (1994). *Reactive Polymers* 22:231-241.

Hutchinson, E. G. and Thornton, J. M. (1996). PROMOTIF: A program to identify and analyze structural motifs in proteins. *Protein Sci* 5:212-220.

Huys, I. et al. (2004). BmTx3, a scorpion toxin with two putative functional faces separately active on A-type K+ and HERG currents. *Biochem J* 378:745-752.

Imperial, J. S. et al. (2007). Using chemistry to reconstruct evolution: On the origins of fish-hunting in the venomous cone snails. *Proc Am Philos Soc*. (in press).

Jacobsen, R. B. et al (1999). Critical residues influence the affinity and selectivity of α-conotoxin MI for nicotinic acetylcholine receptors. *Biochemistry* 38:13310-13315.

Jacobsen, R. B. et al. (2000). Single amino acid substitutions in κ-conotoxin PVIIA disrupt interaction with the Shaker K+ channel. *J Biol Chem* 275:24639-24644.

Johnson, D. S. et al. (1995). α-Conotoxin ImI exhibits subtype specific nicotinic acetylcholine receptor blockade: Preferential inhibition of homomeric α7 and α9 receptors. *Mol Pharmacol* 48:194-199.

Karlin, A. (2002) Emerging structure of the nicotinic acetylcholine receptors. *Nat Rev Neurosci* 3:102-114.

Kaiser et al. (1970). *Anal Biochem* 34:595

Kapoor (1970). *J Pharm Sci* 59:1-27.

Kornreich, W. D. et al. (1986). U.S. Pat. No. 4,569,967.

Laskowski, R. A. et al. (1996). AQUA and PROCHECK-NMR: Programs for checking the quality of protein structures solved by NMR. *J Biomol NMR* 8:477-486.

Luer, M. S. and Hatton, J. (1993). *Annals Pharmcotherapy* 27:912-921.

Lukas, R. J. et al. (1999). International Union of Pharmacology. XX. Current status of the nomenclature for nicotinic acetylcholine receptors and their subunits. *Pharmacol Rev* 51:397-401.

Luo, S. et al. (1998). α-Conotoxin AuIB selectively blocks α3β4 nicotinic acetylcholine receptors and nicotine-evoked norepinephrine release. *J Neurosci* 18:8571-8579.

Marubio, L. M. et al. (1999). Reduced antinociception in mice lacking neuronal nicotinic receptor subunits. *Nature* 398:805-810.

McIntosh, J. M. et al. (1998). *Methods Enzymol* 294:605-624.

McIntosh, J. M. et al. (2005). A novel κ-conotoxin, PeIA, cloned from *Conus pergrandis*, discriminates between rat κ9κ10 and κ7 nicotinic cholinergic receptors. *J Biol Chem* 280:30107-30112.

Miller, C. (1995). The charybdotoxin family of K+ channel blocking peptides. *Neuron* 15:5-10.

Moller, C. et al. (2005) A novel conotoxin framework with a helix-loop-helix (Cs α/α) fold. *Biochemistry* 44:15986-15996.

Mouhat, S. et al. (2004). The functional dyad of scorpion toxin Pi1 is not itself a prerequisite for toxin binding to the voltage-gated Kv1.2 potassium channels. *Biochem. J.* 377: 25-36.

Mukherjee, S. et al. (1994). Serum antibodies to nicotinic acetylcholine receptors in schizophrenic patients. *Schizophrenia Res* 12: 131-136.

Nishiuchi, Y. et al. (1993). *Int. J Pept Protein Res* 42:533-538.

Olamendi-Portugal, T. et al. (2005). Novel α-KTx peptides from the venom of the scorpion Centruroides elegans selectively blockade Kv1.3 over IKCa1 K+ channels of T cells. *Toxicon* 46:418-429.

Olivera, B. M. (1997). *Conus* venom peptides, receptor and ion channel targets and drug design: 50 million years of neuropharmacology (E. E. Just Lecture, 1996). *Mol Biol Cell* 8:2101-2109.

Olivera, B. M. et al. (1984). U.S. Pat. No. 4,447,356.

Olivera; B. M. et al. (1985). Peptide neurotoxins from fish-hunting cone snails. *Science* 230:1338-1343.

Olivera, B. M. et al. (1990). Diversity of *Conus* neuropeptides. *Science* 249:257-263.

Olivera, B. M. et al. (1996). U.S. Pat. No. 5,514,774.

Ornstein, et al. (1993). *Biorganic Medicinal Chemistry Letters* 3:43-48.

Peter, M. J. et al. (2001). Effect of toxins Pi2 and Pi3 on human T lymphocyte Kv1.3 channels: The role of glu7 and lys24. *J Membr Biol* 179:13-25.

*Remington: The Science and Practice of Pharmacy*, 21st Ed., Lippincott Williams & Wilkins, Philadelphia, 2005.

Rivier, J. R. et al. (1987). *Biochem* 26:8508-8512.

Rosengren, K. J. et al. (2003). Twists, knots, and rings in proteins. Structural definition of the cyclotide framework. *J Biol Chem* 278:8606-8616.

Sambrook, J. et al. (1989). *Molecular Cloning: A Laboratory Manual*, 2nd Ed., Cold Spring Harbor Laboratory, Cold Spring Harbor, N.Y.

Schroder and Lubke (1965). *The Peptides* 1:72-75, Academic Press, NY.

Selisko, B. et al. (1998). Cobatoxins 1 and 2 from Centruroides noxius Hoffmann constitute a subfamily of potassium-channel-blocking scorpion toxins. *Eur J Biochem* 254:468-479.

Shon, K. et al. (1998). κ-Conotoxin PVIIA: A peptide inhibiting the Shaker K+ channel. *J Biol Chem* 273:33-38.

Srinivasan, K. N. et al. (2002). κ-Hefutoxin1, a novel toxin from the scorpion Heterometrus fulVipes with unique structure and function. *J Biol Chem* 277:30040-30047.

Steinlein, O. K. et al. (1995). A missense mutation in the neuronal nicotinic acetylcholine receptor alpha subunit is associated with autosomal dominant nocturnal frontal lobe epilepsy. *Nature Genetics* 11:201-203.

Stewart and Young, *Solid-Phase Peptide Synthesis*, Freeman & Co., San Francisco, Calif. (1969).

Terlau, H. et al. (2004) *Conus* venoms: A rich source of novel ion channel-targeted peptides. *Physiol Rev* 84:41-68.

Van de Steen, P. et al. (1998). *Critical Rev. in Biochem. and Mol. Biol.* 33:151-208.

Vale et al. (1978). U.S. Pat. No. 4,105,603.

Verdier, L. et al. (2005). Identification of a novel pharmacophore for peptide toxins interacting with K+ channels. *J Biol Chem* 280:21246-21255.

Wonnacott, S. (1997). Presynaptic nicotinic ACh receptors. *Trends in Neuroscience* 20:92-98.

Wutrich, K. (1986). *NMR of Proteins and Nucleic Acids*, Wiley-Interscience, New York.

Zimm, S. et al. (1984). *Cancer Res* 44:1698-1701.

Zhou L. M. et al. (1996). *J Neurochem* 66:620-628.

---

What is claimed is:

1. An isolated modified J-conotoxin peptide selected from the group consisting of a peptide having the amino acid sequence set forth in SEQ ID NO:2, a peptide having the amino acid sequence set forth in SEQ ID NO:3, a peptide having the amino acid sequence set forth in acid SEQ ID NO:4, a peptide having the amino acid sequence set forth in SEQ ID NO:5, a peptide having the amino acid sequence set forth in SEQ ID NO:6, a peptide having the amino acid sequence set forth in SEQ ID NO:7, a peptide having the amino acid sequence set forth in SEQ ID NO:10, a peptide having the amino acid sequence set forth in SEQ ID NO:11, a peptide having the amino acid sequence set forth in SEQ ID NO:12, a peptide having the amino acid sequence set forth in SEQ ID NO:13, a peptide having the amino acid sequence set forth in SEQ ID NO:14 and a peptide having the amino acid sequence set forth in SEQ ID NO:15, wherein the peptide is modified to contain an O-glycan, an S-glycan or an N-glycan.

2. A pharmaceutical composition comprising a J-conotoxin peptide selected from the group consisting of a peptide having the amino acid sequence set forth in SEQ ID NO:2, a peptide having the amino acid sequence set forth in SEQ ID NO:3, a peptide having the amino acid sequence set forth in SEQ ID NO:4, a peptide having the amino acid sequence set forth in SEQ ID NO:5, a peptide having the amino acid sequence set forth in SEQ ID NO:6, a peptide having the amino acid sequence set forth in SEQ ID NO:7, a peptide having the amino acid sequence set forth in SEQ ID NO:10, a peptide having the amino acid sequence set forth in SEQ ID NO:11, a peptide having the amino acid sequence set forth in SEQ ID NO:12, a peptide having the amino acid sequence set forth in SEQ ID NO:13, a peptide having the amino acid sequence set forth in SEQ ID NO:14 and a peptide having the amino acid sequence set forth in SEQ ID NO:15 or a pharmaceutically acceptable salt or solvate thereof and a pharmaceutically acceptable carrier wherein the peptide is modified to contain an O-glycan, an S-glycan or an N-glycan.

3. A method of selecting for a compound that mimics the therapeutic activity of a J-conotoxin peptide, comprising the steps of: (a) conducting a biological assay on a test compound to determine the therapeutic activity; (b) conducting the same biological assay on a J-conotoxin peptide; and (c) selecting a test compound that has the same assay results as the J-conotoxin peptide as a compound that mimics the therapeutic activity of a J-conotoxin peptide, wherein the J-conotoxin peptide is selected from the group consisting of a peptide having the amino acid sequence set forth in SEQ NO:2, a peptide having the amino acid sequence set forth in SEQ ID NO:3, a peptide having the amino acid sequence set forth in SEQ ID NO:4, a peptide having the amino acid sequence set forth in SEQ ID NO:5, a peptide having the amino acid sequence set forth in SEQ ID NO:6, a peptide having the amino acid sequence set forth in SEQ ID NO:7, a peptide having the amino acid sequence set forth in SEQ ID NO:10, a peptide having the amino acid sequence set forth in SEQ ID NO:11, a peptide having the amino acid sequence set forth in SEQ ID NO:12, a peptide having the amino acid sequence set forth in SEQ ID NO:13, a peptide having the amino acid sequence set forth in SEQ ID NO:14 and a peptide having the amino acid sequence set forth in SEQ ID NO:15 of claim 1.

4. The pharmaceutical composition of claim 3, wherein the peptide is a peptide having the amino acid sequence set forth in SEQ ID NO:2.

5. The pharmaceutical composition of claim 3, wherein the peptide is a peptide having the amino acid sequence set forth in SEQ ED NO:3.

6. The pharmaceutical composition of claim 3, wherein the peptide is a peptide having the amino acid sequence set forth in SEQ ID NO:4.

7. The pharmaceutical composition of claim 3, wherein the peptide is a peptide having the amino acid sequence set forth in SEQ ID NO:5.

8. The pharmaceutical composition of claim 3, wherein the peptide is a peptide having the amino acid sequence set forth in SEQ ID NO:6.

9. The pharmaceutical composition of claim 3, wherein the peptide is a peptide having the amino acid sequence set forth in SEQ ID NO:7.

10. The pharmaceutical composition of claim 3, wherein the peptide is a peptide having the amino acid sequence set forth in SEQ ID NO:10.

11. The pharmaceutical composition of claim 3, wherein the peptide is a peptide having the amino acid sequence set forth in SEQ ID NO:11.

12. The pharmaceutical composition of claim 3, wherein the peptide is a peptide having the amino acid sequence set forth in SEQ ID NO:12.

13. The pharmaceutical composition of claim 3, wherein the peptide is a peptide having the amino acid sequence set forth in SEQ ID NO:13.

14. The pharmaceutical composition of claim 3, wherein the peptide is a peptide having the amino acid sequence set forth in SEQ ID NO:14.

15. The pharmaceutical composition of claim 3, wherein the peptide is a peptide having the amino acid sequence set forth in SEQ ID NO:15.

* * * * *

SEQUENCE LISTING

<160> NUMBER OF SEQ ID NOS: 51

<210> SEQ ID NO 1
<211> LENGTH: 25
<212> TYPE: PRT
<213> ORGANISM: Artificial
<220> FEATURE:
<223> OTHER INFORMATION: Generic J-Superfamily Conotoxin Peptide
<220> FEATUR -continued

```
<222> LOCATION: (1)..(2)
<223> OTHER INFORMATION: Xaa at residue 1 is Phe, Gly, Ser, Thr, g-Ser
      (where g is glycosylation), g-Thr or any synthetic hydroxylated
      amino acid; Xaa at residue 2 is Pro, hydroxy-Pro (Hyp), Ser, Thr,
      g-Ser, g-Thr or any synthetic hydroxylated amino acid.
<220> FEATURE:
<221> NAME/KEY: PEPTIDE
<222> LOCATION: (3)..(3)
<223> OTHER INFORMATION: Xaa at residue 3 is Gly, Arg, Lys, ornithine,
      homo-Lys, homoarginine, nor-Lys, N-methyl-Lys, N,N'-dimethyl-Lys,
      N,N',N''-trimethyl-Lys or any synthetic basic amino acid.
<220> FEATURE:
<221> NAME/KEY: PEPTIDE
<222> LOCATION: (4)..(4)
<223> OTHER INFORMATION: Xaa at residue 4 is Pro, hydroxy-Pro (Hyp),
      Ser, Thr, g-Ser, g-Thr or any synthetic hydroxylated amino acid.
<220> FEATURE:
<221> NAME/KEY: PEPTIDE
<222> LOCATION: (5)..(5)
<223> OTHER INFORMATION: Xaa at residue 5 is Ala, Thr, g-Thr, Ser,
      g-Ser, any synthetic hydroxylated amino acid, Arg, Lys, ornithine,
      homo-Lys, homoarginine, nor-Lys, N-methyl-Lys, N,N'-dimethyl-Lys,
      N,N',N''-trimethyl-Lys or any synthetic basic amino acid.
<220> FEATURE:
<221> NAME/KEY: PEPTIDE
<222> LOCATION: (6)..(6)
<223> OTHER INFORMATION: Xaa at residue 6 is an aliphatic amino acid
      bearing linear or branched saturated hydrocarbon chains such as
      Leu (D or L), Ile and Val or non-natural derivatives of the
      aliphatic amino acid.
<220> FEATURE:
<221> NAME/KEY: PEPTIDE
<222> LOCATION: (8)..(8)
<223> OTHER INFORMATION: Xaa at residue 8 is Asn, Gln, Lys, Arg,
      ornithine, homo-Lys, homoarginine, nor-Lys, N-methyl-Lys,
      N,N'-dimethyl-Lys, N,N',N''-trimethyl-Lys or any synthetic basic
      amino acid.
<220> FEATURE:
<221> NAME/KEY: PEPTIDE
<222> LOCATION: (9)..(10)
<223> OTHER INFORMATION: Xaa at residue 9 is Met, an aliphatic amino
      acid bearing linear or branched saturated hydrocarbon chains such
      as Leu (D or L), Ile and Val or non-natural derivatives of the
      aliphatic amino acid; Xaa at residue 10 is Ala or Met.
<220> FEATURE:
<221> NAME/KEY: PEPTIDE
<222> LOCATION: (12)..(12)
<223> OTHER INFORMATION: Xaa at residue 12 is Arg, Lys, ornithine,
      homo-Lys, homoarginine, nor-Lys, N-methyl-Lys, N,N'-dimethyl-Lys,
      N,N',N''-trimethyl-Lys or any synthetic basic amino acid.
<220> FEATURE:
<221> NAME/KEY: PEPTIDE
<222> LOCATION: (13)..(13)
<223> OTHER INFORMATION: Xaa at residue 13 is Ala, Thr, g-Thr, Ser,
      g-Ser, any synthetic hydroxylated amino acid, an aliphatic amino
      acid bearing linear or branched saturated hydrocarbon chains such
      as Leu (D or L), Ile and Val or non-natural derivatives of the
      aliphatic amino
<220> FEATURE:
<221> NAME/KEY: PEPTIDE
<222> LOCATION: (14)..(15)
<223> OTHER INFORMATION: Xaa at residue 14 is Gly, Glu, Asp or any
      synthetic acidic amino acid; Xaa at residue 15 is Gln, Asn, His,
      Tyr, meta-Tyr, ortho-Tyr, nor-Tyr, mono-halo-Tyr, di-halo-Tyr,
      O-sulpho-Tyr, O-phospho-Tyr, nitro-Tyr, an aliphatic amino acids
      bearing linear
<220> FEATURE:
<221> NAME/KEY: PEPTIDE
<222> LOCATION: (15)..(17)
<223> OTHER INFORMATION: saturated hydrocarbon chains such as Leu
      (D or L), Ile and Val or non-natural derivatives of the aliphatic
      amino acid; Xaa at residue 16 is Gly; Xaa at residue 17 is His.
<220> FEATURE:
<221> NAME/KEY: PEPTIDE
<222> LOCATION: (18)..(18)
<223> OTHER INFORMATION: Xaa at residue 18 is Met, Lys, Arg, ornithine,
      homo-Lys, homoarginine, nor-Lys, N-methyl-Lys, N,N'-dimethyl-Lys,
      N,N',N''-trimethyl-Lys, any synthetic basic amino acid, an
      aliphatic amino acid bearing linear or branched saturated
```

```
<220> FEATURE:
<221> NAME/KEY: PEPTIDE
<222> LOCATION: (18)..(19)
<223> OTHER INFORMATION: Leu (D or L), Ile and Val or non-natural
      derivatives of the aliphatic amino acid; Xaa at residue 19 is Tyr,
      meta-Tyr, ortho-Tyr, nor-Tyr, mono-halo-Tyr, di-halo-Tyr,
      O-sulpho-Tyr, O-phospho-Tyr or nitro-Tyr.
<220> FEATURE:
<221> NAME/KEY: PEPTIDE
<222> LOCATION: (20)..(23)
<223> OTHER INFORMATION: Xaa at residue 20 is Pro or Hyp; Xaa at residue
      21 is Phe, Ser, Thr, g-Ser, g-Thr or any synthetic hydroxylated
      amino acid; Xaa at residue 23 is His, Gly, Asn or Gln.
<220> FEATURE:
<221> NAME/KEY: PEPTIDE
<222> LOCATION: (25)..(25)
<223> OTHER INFORMATION: Xaa at residue 25 is Asn, Gln, Glu, Gla, Asp,
      any synthetic acidic amino acid, Arg, Lys, ornithine, homo-Lys,
      homoarginine, nor-Lys, N-methyl-Lys, N,N'-dimethyl-Lys, N,N',N''-
      trimethyl-Lys or any synthetic basic amino acid.

<400> SEQUENCE: 1

Xaa Xaa Xaa Xaa Xaa Xaa Cys Xaa Xaa Xaa Cys Xaa Xaa Xaa Xaa
1               5                   10                  15

Xaa Xaa Xaa Xaa Xaa Cys Xaa Cys Xaa
            20                  25

<210> SEQ ID NO 2
<211> LENGTH: 25
<212> TYPE: PRT
<213> ORGANISM: Conus planorbis
<220> FEATURE:
<221> NAME/KEY: PEPTIDE
<222> LOCATION: (1)..(25)
<223> OTHER INFORMATION: Xaa at residues 2, 4 and 20 is Pro or hydroxy-
      Pro; Xaa at residue 19 is Tyr, 125I-Tyr, mono-iodo-Tyr, di-iodo-
      Tyr, O-sulpho-Tyr or O-phospho-Tyr.

<400> SEQUENCE: 2

Phe Xaa Arg Xaa Arg Ile Cys Asn Leu Ala Cys Arg Ala Gly Ile Gly
1               5                   10                  15

His Lys Xaa Xaa Phe Cys His Cys Arg
            20                  25

<210> SEQ ID NO 3
<211> LENGTH: 25
<212> TYPE: PRT
<213> ORGANISM: Conus planorbis
<220> FEATURE:
<221> NAME/KEY: PEPTIDE
<222> LOCATION: (1)..(25)
<223> OTHER INFORMATION: Xaa at residues 2 and 20 is Pro or hydroxy-Pro;
      Xaa at residue 19 is Tyr, 125I-Tyr, mono-iodo-Tyr, di-iodo-Tyr,
      O-sulpho-Tyr or O-phospho-Tyr.

<400> SEQUENCE: 3

Gly Xaa Gly Ser Ala Ile Cys Asn Met Ala Cys Arg Leu Gly Gln Gly
1               5                   10                  15

His Met Xaa Xaa Phe Cys Asn Cys Asn
            20                  25

<210> SEQ ID NO 4
<211> LENGTH: 25
<212> TYPE: PRT
<213> ORGANISM: Conus planorbis
<220> FEATURE:
<221> NAME/KEY: PEPTIDE
<222> LOCATION: (1)..(25)
<223> OTHER INFORMATION: Xaa at residues 2 and 20 is Pro or hydroxy-Pro;
      Xaa at residue 14 is Glu or gamma-carboxy-Glu; Xaa at residue 19
```

-continued is Tyr, 125I-Tyr, mono-iodo-Tyr, di-iodo-Tyr, O-sulpho-Tyr or O-
phospho-Tyr.

<400> SEQUENCE: 4

Gly Xaa Gly Ser Ala Ile Cys Asn Met Ala Cys Arg Leu Xaa His Gly
1               5                   10                  15

His Leu Xaa Xaa Phe Cys His Cys Arg
            20                  25

<210> SEQ ID NO 5
<211> LENGTH: 25
<212> TYPE: PRT
<213> ORGANISM: Conus planorbis
<220> FEATURE:
<221> NAME/KEY: PEPTIDE
<222> LOCATION: (1)..(25)
<223> OTHER INFORMATION: Xaa at residues 2 and 20 is Pro or hydroxy-Pro;
      Xaa at residue 14 is Glu or gamma-carboxy-Glu; Xaa at residue 19
      is Tyr, 125I-Tyr, mono-iodo-Tyr, di-iodo-Tyr, O-sulpho-Tyr or
      O-phospho-Tyr.

<400> SEQUENCE: 5

Gly Xaa Gly Ser Ala Ile Cys Asn Met Ala Cys Arg Leu Xaa His Gly
1               5                   10                  15

His Leu Xaa Xaa Phe Cys Asn Cys Asp
            20                  25

<210> SEQ ID NO 6
<211> LENGTH: 25
<212> TYPE: PRT
<213> ORGANISM: Conus ferrugineus
<220> FEATURE:
<221> NAME/KEY: PEPTIDE
<222> LOCATION: (1)..(25)
<223> OTHER INFORMATION: Xaa at residues 2 and 20 is Pro or hydroxy-Pro;
      Xaa at residue 19 is Tyr, 125I-Tyr, mono-iodo-Tyr, di-iodo-Tyr,
      O-sulpho-Tyr or O-phospho-Tyr.

<400> SEQUENCE: 6

Ser Xaa Gly Ser Thr Ile Cys Lys Met Ala Cys Arg Thr Gly Asn Gly
1               5                   10                  15

His Lys Xaa Xaa Phe Cys Asn Cys Arg
            20                  25

<210> SEQ ID NO 7
<211> LENGTH: 25
<212> TYPE: PRT
<213> ORGANISM: Conus ferrugineus
<220> FEATURE:
<221> NAME/KEY: PEPTIDE
<222> LOCATION: (1)..(25)
<223> OTHER INFORMATION: Xaa at residues 15 and 19 is Tyr, 125I-Tyr,
      mono-iodo-Tyr, di-iodo-Tyr, O-sulpho-Tyr or O-phospho-Tyr; Xaa
      at residue 20 is Pro or hydroxy-Pro.

<400> SEQUENCE: 7

Ser Ser Gly Ser Thr Val Cys Lys Met Met Cys Arg Leu Gly Xaa Gly
1               5                   10                  15

His Leu Xaa Xaa Ser Cys Gly Cys Arg
            20                  25

<210> SEQ ID NO 8
<211> LENGTH: 201
<212> TYPE: DNA
<213> ORGANISM: Conus planorbis
<220> FEATURE:
<221> NAME/KEY: CDS

<222> LOCATION: (1)..(201)

<400> SEQUENCE: 8

| atg | ccg | tct | gtt | cgg | tct | gtg | acc | tgc | tgc | tgt | ctg | ctg | tgg | atg | atg | 48 |
|---|---|---|---|---|---|---|---|---|---|---|---|---|---|---|---|---|
| Met | Pro | Ser | Val | Arg | Ser | Val | Thr | Cys | Cys | Cys | Leu | Leu | Trp | Met | Met | |
| 1 | | | | 5 | | | | | 10 | | | | | 15 | | |

| ttc | tct | gta | cag | ctc | gtc | act | cct | ggc | tcc | cct | gga | act | gca | cag | ctg | 96 |
|---|---|---|---|---|---|---|---|---|---|---|---|---|---|---|---|---|
| Phe | Ser | Val | Gln | Leu | Val | Thr | Pro | Gly | Ser | Pro | Gly | Thr | Ala | Gln | Leu | |
| | | | 20 | | | | | 25 | | | | | 30 | | | |

| tct | ggg | cat | cgc | act | gct | aga | ttt | cct | aga | ccg | aga | ata | tgc | aat | ctg | 144 |
|---|---|---|---|---|---|---|---|---|---|---|---|---|---|---|---|---|
| Ser | Gly | His | Arg | Thr | Ala | Arg | Phe | Pro | Arg | Pro | Arg | Ile | Cys | Asn | Leu | |
| | | 35 | | | | | 40 | | | | | 45 | | | | |

| gcg | tgc | agg | gcg | gga | atc | gga | cac | aag | tat | ccc | ttt | tgc | cat | tgc | aga | 192 |
|---|---|---|---|---|---|---|---|---|---|---|---|---|---|---|---|---|
| Ala | Cys | Arg | Ala | Gly | Ile | Gly | His | Lys | Tyr | Pro | Phe | Cys | His | Cys | Arg | |
| 50 | | | | | 55 | | | | | 60 | | | | | | |

| ggg | aaa | cgg | | | | | | | | | | | | | | 201 |
|---|---|---|---|---|---|---|---|---|---|---|---|---|---|---|---|---|
| Gly | Lys | Arg | | | | | | | | | | | | | | |
| 65 | | | | | | | | | | | | | | | | |

<210> SEQ ID NO 9
<211> LENGTH: 67
<212> TYPE: PRT
<213> ORGANISM: Conus planorbis

<400> SEQUENCE: 9

Met Pro Ser Val Arg Ser Val Thr Cys Cys Cys Leu Leu Trp Met Met
1               5                   10                  15

Phe Ser Val Gln Leu Val Thr Pro Gly Ser Pro Gly Thr Ala Gln Leu
            20                  25                  30

Ser Gly His Arg Thr Ala Arg Phe Pro Arg Pro Arg Ile Cys Asn Leu
        35                  40                  45

Ala Cys Arg Ala Gly Ile Gly His Lys Tyr Pro Phe Cys His Cys Arg
    50                  55                  60

Gly Lys Arg
65

<210> SEQ ID NO 10
<211> LENGTH: 25
<212> TYPE: PRT
<213> ORGANISM: Conus planorbis

<400> SEQUENCE: 10

Phe Pro Arg Pro Arg Ile Cys Asn Leu Ala Cys Arg Ala Gly Ile Gly
1               5                   10                  15

His Lys Tyr Pro Phe Cys His Cys Arg
            20                  25

<210> SEQ ID NO 11
<211> LENGTH: 25
<212> TYPE: PRT
<213> ORGANISM: Conus planorbis

<400> SEQUENCE: 11

Gly Pro Gly Ser Ala Ile Cys Asn Met Ala Cys Arg Leu Gly Gln Gly
1               5                   10                  15

His Met Tyr Pro Phe Cys Asn Cys Asn
            20                  25

<210> SEQ ID NO 12
<211> LENGTH: 25
<212> TYPE: PRT

<213> ORGANISM: Conus planorbis

<400> SEQUENCE: 12

Gly Pro Gly Ser Ala Ile Cys Asn Met Ala Cys Arg Leu Glu His Gly
1               5                   10                  15
His Leu Tyr Pro Phe Cys His Cys Arg
            20                  25

<210> SEQ ID NO 13
<211> LENGTH: 25
<212> TYPE: PRT
<213> ORGANISM: Conus planorbis

<400> SEQUENCE: 13

Gly Pro Gly Ser Ala Ile Cys Asn Met Ala Cys Arg Leu Glu His Gly
1               5                   10                  15
His Leu Tyr Pro Phe Cys Asn Cys Asp
            20                  25

<210> SEQ ID NO 14
<211> LENGTH: 25
<212> TYPE: PRT
<213> ORGANISM: Conus ferrugineus

<400> SEQUENCE: 14

Ser Pro Gly Ser Thr Ile Cys Lys Met Ala Cys Arg Thr Gly Asn Gly
1               5                   10                  15
His Lys Tyr Pro Phe Cys Asn Cys Arg
            20                  25

<210> SEQ ID NO 15
<211> LENGTH: 25
<212> TYPE: PRT
<213> ORGANISM: Conus ferrugineus

<400> SEQUENCE: 15

Ser Ser Gly Ser Thr Val Cys Lys Met Met Cys Arg Leu Gly Tyr Gly
1               5                   10                  15
His Leu Tyr Pro Ser Cys Gly Cys Arg
            20                  25

<210> SEQ ID NO 16
<211> LENGTH: 7
<212> TYPE: PRT
<213> ORGANISM: Conus planorbis

<400> SEQUENCE: 16

Gly Ile Gly His Lys Tyr Pro
1               5

<210> SEQ ID NO 17
<211> LENGTH: 19
<212> TYPE: DNA
<213> ORGANISM: Artificial
<220> FEATURE:
<223> OTHER INFORMATION: Oligonucleotide PCR primer
<220> FEATURE:
<221> NAME/KEY: misc_feature
<222> LOCATION: (1)..(19)
<223> OTHER INFORMATION: n may be any base

<400> SEQUENCE: 17
ggnathggnc ayaaatatc                                            19

```
<210> SEQ ID NO 18
<211> LENGTH: 8
<212> TYPE: PRT
<213> ORGANISM: Conus planorbis

<400> SEQUENCE: 18

His Lys Tyr Pro Phe Cys His Cys
1               5

<210> SEQ ID NO 19
<211> LENGTH: 23
<212> TYPE: DNA
<213> ORGANISM: Artificial
<220> FEATURE:
<223> OTHER INFORMATION: Oligonucleotide PCR primer
<220> FEATURE:
<221> NAME/KEY: misc_feature
<222> LOCATION: (1)..(23)
<223> OTHER INFORMATION: n may be any base

<400> SEQUENCE: 19
cayaartayc cnttytgyca ytg                                            23

<210> SEQ ID NO 20
<211> LENGTH: 25
<212> TYPE: DNA
<213> ORGANISM: Artificial
<220> FEATURE:
<223> OTHER INFORMATION: Oligonucleotide PCR primer

<400> SEQUENCE: 20
gcgtcattgg aatgagtatg ccgtc                                          25

<210> SEQ ID NO 21
<211> LENGTH: 25
<212> TYPE: DNA
<213> ORGANISM: Artificial
<220> FEATURE:
<223> OTHER INFORMATION: Oligonucleotide PCR primer

<400> SEQUENCE: 21
ccgcgtcccg tttccctctg caatg                                          25

<210> SEQ ID NO 22
<211> LENGTH: 23
<212> TYPE: DNA
<213> ORGANISM: Artificial
<220> FEATURE:
<223> OTHER INFORMATION: Oligonucleotide PCR primer

<400> SEQUENCE: 22
ccatgccgtc tgttcggtct gtg                                            23

<210> SEQ ID NO 23
<211> LENGTH: 4
<212> TYPE: PRT
<213> ORGANISM: Conus planorbis

<400> SEQUENCE: 23

Arg Gly Lys Arg
1

<210> SEQ ID NO 24
<211> LENGTH: 24
<212> TYPE: PRT
<213> ORGANISM: Conus planorbis
```

```
<400> SEQUENCE: 24

Met Pro Ser Val Arg Ser Val Thr Cys Cys Leu Leu Trp Met Met
1               5                   10                  15

Phe Ser Val Gln Leu Val Thr Pro
            20

<210> SEQ ID NO 25
<211> LENGTH: 4
<212> TYPE: PRT
<213> ORGANISM: Conus planorbis

<400> SEQUENCE: 25

Cys Gly Lys Arg
1

<210> SEQ ID NO 26
<211> LENGTH: 29
<212> TYPE: PRT
<213> ORGANISM: Conus geographus
<220> FEATURE:
<221> NAME/KEY: PEPTIDE
<222> LOCATION: (9)..(9)
<223> OTHER INFORMATION: Xaa at residue 9 is gamma-carboxy-Glu.

<400> SEQUENCE: 26

Lys Phe Leu Ser Gly Gly Phe Tyr Xaa Ile Val Cys His Arg Tyr Cys
1               5                   10                  15

Ala Lys Gly Ile Ala Lys Glu Phe Cys Asn Cys Pro Asp
            20                  25

<210> SEQ ID NO 27
<211> LENGTH: 27
<212> TYPE: PRT
<213> ORGANISM: Conus floridanus floridensis

<400> SEQUENCE: 27

Trp Asp Val Asn Asp Cys Ile His Phe Cys Leu Ile Gly Val Val Glu
1               5                   10                  15

Arg Ser Tyr Thr Glu Cys His Thr Met Cys Thr
            20                  25

<210> SEQ ID NO 28
<211> LENGTH: 27
<212> TYPE: PRT
<213> ORGANISM: Conus floridanus floridensis

<400> SEQUENCE: 28

Trp Asp Val Asn Asp Cys Ile His Phe Cys Leu Ile Gly Val Val Gly
1               5                   10                  15

Arg Ser Tyr Thr Glu Cys His Thr Met Cys Thr
            20                  25

<210> SEQ ID NO 29
<211> LENGTH: 27
<212> TYPE: PRT
<213> ORGANISM: Conus floridanus floridensis

<400> SEQUENCE: 29

Trp Asp Ala Tyr Asp Cys Ile Gln Phe Cys Met Arg Pro Glu Met Arg
1               5                   10                  15

His Thr Tyr Ala Gln Cys Leu Ser Ile Cys Thr
            20                  25
```

<210> SEQ ID NO 30
<211> LENGTH: 27
<212> TYPE: PRT
<213> ORGANISM: Conus villepinii

<400> SEQUENCE: 30

Gly Gly Leu Gly Arg Cys Ile Tyr Asn Cys Met Asn Ser Gly Gly
1               5                   10                  15

Leu Ser Phe Ile Gln Cys Lys Thr Met Cys Tyr
            20                  25

<210> SEQ ID NO 31
<211> LENGTH: 14
<212> TYPE: PRT
<213> ORGANISM: Conus magus

<400> SEQUENCE: 31

Gly Arg Cys Cys His Pro Ala Cys Gly Lys Asn Tyr Ser Cys
1               5                   10

<210> SEQ ID NO 32
<211> LENGTH: 13
<212> TYPE: PRT
<213> ORGANISM: Conus geographus

<400> SEQUENCE: 32

Glu Cys Cys Asn Pro Ala Cys Gly Arg His Tyr Ser Cys
1               5                   10

<210> SEQ ID NO 33
<211> LENGTH: 13
<212> TYPE: PRT
<213> ORGANISM: Conus striatus

<400> SEQUENCE: 33

Ile Cys Cys Asn Pro Ala Cys Gly Pro Lys Tyr Ser Cys
1               5                   10

<210> SEQ ID NO 34
<211> LENGTH: 15
<212> TYPE: PRT
<213> ORGANISM: Conus aulicus

<400> SEQUENCE: 34

Gly Cys Cys Ser Tyr Pro Pro Cys Phe Ala Thr Asn Pro Asp Cys
1               5                   10                  15

<210> SEQ ID NO 35
<211> LENGTH: 16
<212> TYPE: PRT
<213> ORGANISM: Conus pergrandis

<400> SEQUENCE: 35

Gly Cys Cys Ser His Pro Ala Cys Ser Val Asn His Pro Glu Leu Cys
1               5                   10                  15

<210> SEQ ID NO 36
<211> LENGTH: 13
<212> TYPE: PRT
<213> ORGANISM: Conus bullatus

<400> SEQUENCE: 36

Gly Cys Cys Ser Thr Pro Pro Cys Ala Val Leu Tyr Cys

<210> SEQ ID NO 37
<211> LENGTH: 603
<212> TYPE: DNA
<213> ORGANISM: Conus planorbis
<220> FEATURE:
<221> NAME/KEY: CDS
<222> LOCATION: (7)..(234)

<400> SEQUENCE: 37

```
agcacc atg ccg tct gtt cgg tct gtg acc tgc tgc tgt ctg ctg tgg       48
       Met Pro Ser Val Arg Ser Val Thr Cys Cys Cys Leu Leu Trp
       1               5                   10 atg atg ttc tct gta cag ctc gtc act cct ggc tcc cct gga act gca       96
Met Met Phe Ser Val Gln Leu Val Thr Pro Gly Ser Pro Gly Thr Ala
15                  20                  25                  30 cag ctg tct ggg cat cgc act gct aga ttt cct aga ccg aga ata tgc      144
Gln Leu Ser Gly His Arg Thr Ala Arg Phe Pro Arg Pro Arg Ile Cys
                35                  40                  45 aat ctg gcg tgc agg gcg gga atc gga cac aag tat ccc ttt tgc cat      192
Asn Leu Ala Cys Arg Ala Gly Ile Gly His Lys Tyr Pro Phe Cys His
            50                  55                  60 tgc aga ggg aaa cgg gac gcg gtt tct tca tcg atg gcg gtt              234
Cys Arg Gly Lys Arg Asp Ala Val Ser Ser Ser Met Ala Val
65                  70                  75 tgacggcata ctcattccaa tgacgcagac accattcgct gggattgaaa gcctctcttc    294
aaaaatcttc tctggtctag aattgccagt ccaaaaatat cccaatactc ccagtgtctg    354
ccaagtcgtg tgatgcccta aaagtactca agagtatggt gtggtacacc atctcatgtt    414
atcctatata tcctcaagtc tgtgtcttga ttttccaccc acaattcgct tctccatata    474
atgataggcc tatgccttga tacccccacg tccttagtgt atgtcctgat accccatatg    534
tccttcattc tatctcctga tgcctcatac ttttgtgatt aaaatatgaa gacagcaaaa    594
aaaaaaaaa                                                            603
```

<210> SEQ ID NO 38
<211> LENGTH: 76
<212> TYPE: PRT
<213> ORGANISM: Conus planorbis

<400> SEQUENCE: 38

```
Met Pro Ser Val Arg Ser Val Thr Cys Cys Cys Leu Leu Trp Met Met
1               5                   10                  15

Phe Ser Val Gln Leu Val Thr Pro Gly Ser Pro Gly Thr Ala Gln Leu
            20                  25                  30

Ser Gly His Arg Thr Ala Arg Phe Pro Arg Pro Arg Ile Cys Asn Leu
        35                  40                  45

Ala Cys Arg Ala Gly Ile Gly His Lys Tyr Pro Phe Cys His Cys Arg
    50                  55                  60

Gly Lys Arg Asp Ala Val Ser Ser Ser Met Ala Val
65                  70                  75
```

<210> SEQ ID NO 39
<211> LENGTH: 231
<212> TYPE: DNA
<213> ORGANISM: Conus planorbis
<220> FEATURE:
<221> NAME/KEY: CDS
<222> LOCATION: (1)..(228)

<400> SEQUENCE: 39

```
atg ccg tct gtt cgg tct gtg acc tgc tgc tgt ctg ctg tgg atg atg      48
Met Pro Ser Val Arg Ser Val Thr Cys Cys Cys Leu Leu Trp Met Met
1               5                   10                  15 ctc tct gtg cag ctc gtc act cct ggc tcc cct gca act gca cag ctg      96
Leu Ser Val Gln Leu Val Thr Pro Gly Ser Pro Ala Thr Ala Gln Leu
            20                  25                  30 tct ggg cag cgc act gct aga ggt cct gga tcg gca ata tgc aat atg      144
Ser Gly Gln Arg Thr Ala Arg Gly Pro Gly Ser Ala Ile Cys Asn Met
        35                  40                  45 gcg tgc agg ttg gga cag gga cac atg tat ccc ttt tgc aat tgc aat      192
Ala Cys Arg Leu Gly Gln Gly His Met Tyr Pro Phe Cys Asn Cys Asn
    50                  55                  60 ggg aaa cgg gac gtg gtt tct tca tcg atg gcg gtg tga                  231
Gly Lys Arg Asp Val Val Ser Ser Ser Met Ala Val
65                  70                  75
```

<210> SEQ ID NO 40
<211> LENGTH: 76
<212> TYPE: PRT
<213> ORGANISM: Conus planorbis

<400> SEQUENCE: 40

```
Met Pro Ser Val Arg Ser Val Thr Cys Cys Cys Leu Leu Trp Met Met
1               5                   10                  15

Leu Ser Val Gln Leu Val Thr Pro Gly Ser Pro Ala Thr Ala Gln Leu
            20                  25                  30

Ser Gly Gln Arg Thr Ala Arg Gly Pro Gly Ser Ala Ile Cys Asn Met
        35                  40                  45

Ala Cys Arg Leu Gly Gln Gly His Met Tyr Pro Phe Cys Asn Cys Asn
    50                  55                  60

Gly Lys Arg Asp Val Val Ser Ser Ser Met Ala Val
65                  70                  75
```

<210> SEQ ID NO 41
<211> LENGTH: 204
<212> TYPE: DNA
<213> ORGANISM: Conus planorbis
<220> FEATURE:
<221> NAME/KEY: CDS
<222> LOCATION: (1)..(204)

<400> SEQUENCE: 41

```
atg ccg tct gtt cgg tct gtg acc tgc tgc tgt ctg ctg tgg atg atg      48
Met Pro Ser Val Arg Ser Val Thr Cys Cys Cys Leu Leu Trp Met Met
1               5                   10                  15 ttc tct gta cag ctc gtc act cct ggc tcc cct gca act gca cag ctg      96
Phe Ser Val Gln Leu Val Thr Pro Gly Ser Pro Ala Thr Ala Gln Leu
            20                  25                  30 tct ggg cag cgc act gct aga ggt cct gga tcg gca ata tgc aat atg      144
Ser Gly Gln Arg Thr Ala Arg Gly Pro Gly Ser Ala Ile Cys Asn Met
        35                  40                  45 gcg tgc agg ttg gaa cac gga cac ctg tat ccc ttt tgc cat tgc aga      192
Ala Cys Arg Leu Glu His Gly His Leu Tyr Pro Phe Cys His Cys Arg
    50                  55                  60 ggg aaa cgg gac                                                       204
Gly Lys Arg Asp
65
```

<210> SEQ ID NO 42
<211> LENGTH: 68

-continued

```
<212> TYPE: PRT
<213> ORGANISM: Conus planorbis

<400> SEQUENCE: 42

Met Pro Ser Val Arg Ser Val Thr Cys Cys Cys Leu Leu Trp Met Met
1               5                   10                  15

Phe Ser Val Gln Leu Val Thr Pro Gly Ser Pro Ala Thr Ala Gln Leu
            20                  25                  30

Ser Gly Gln Arg Thr Ala Arg Gly Pro Gly Ser Ala Ile Cys Asn Met
        35                  40                  45

Ala Cys Arg Leu Glu His Gly His Leu Tyr Pro Phe Cys His Cys Arg
    50                  55                  60

Gly Lys Arg Asp
65

<210> SEQ ID NO 43
<211> LENGTH: 231
<212> TYPE: DNA
<213> ORGANISM: Conus planorbis
<220> FEATURE:
<221> NAME/KEY: CDS
<222> LOCATION: (1)..(228)

<400> SEQUENCE: 43 atg ccg tct gtt cgg tct gtg gcc tgc tgc tgt ctg ctg tgg atg atg      48
Met Pro Ser Val Arg Ser Val Ala Cys Cys Cys Leu Leu Trp Met Met
1               5                   10                  15 ctc tct gta cag ctc gtc act cct ggc tcc cct gca act gca cag ctg      96
Leu Ser Val Gln Leu Val Thr Pro Gly Ser Pro Ala Thr Ala Gln Leu
            20                  25                  30 tct ggg cag cgc act gct aga ggt cct gga tcg gca ata tgc aat atg     144
Ser Gly Gln Arg Thr Ala Arg Gly Pro Gly Ser Ala Ile Cys Asn Met
        35                  40                  45 gcg tgc agg ttg gaa cac gga cac ctg tat ccc ttt tgc aat tgc gat     192
Ala Cys Arg Leu Glu His Gly His Leu Tyr Pro Phe Cys Asn Cys Asp
    50                  55                  60 ggg aaa cgg gac gtg gtt tct tca tcg atg gcg gtg tga                 231
Gly Lys Arg Asp Val Val Ser Ser Ser Met Ala Val
65                  70                  75

<210> SEQ ID NO 44
<211> LENGTH: 76
<212> TYPE: PRT
<213> ORGANISM: Conus planorbis

<400> SEQUENCE: 44

Met Pro Ser Val Arg Ser Val Ala Cys Cys Cys Leu Leu Trp Met Met
1               5                   10                  15

Leu Ser Val Gln Leu Val Thr Pro Gly Ser Pro Ala Thr Ala Gln Leu
            20                  25                  30

Ser Gly Gln Arg Thr Ala Arg Gly Pro Gly Ser Ala Ile Cys Asn Met
        35                  40                  45

Ala Cys Arg Leu Glu His Gly His Leu Tyr Pro Phe Cys Asn Cys Asp
    50                  55                  60

Gly Lys Arg Asp Val Val Ser Ser Ser Met Ala Val
65                  70                  75

<210> SEQ ID NO 45
<211> LENGTH: 231
<212> TYPE: DNA
<213> ORGANISM: Conus ferrugineus
```

```
<220> FEATURE:
<221> NAME/KEY: CDS
<222> LOCATION: (1)..(228)

<400> SEQUENCE: 45 atg ccg tct gtt cgg tct gtg acc tgc tgc tgt ctg ctg tgg atg atg      48
Met Pro Ser Val Arg Ser Val Thr Cys Cys Cys Leu Leu Trp Met Met
1               5                   10                  15 ctc tct gta cag ctc gtc act cct ggc tcc cct gga act gca cag ctg      96
Leu Ser Val Gln Leu Val Thr Pro Gly Ser Pro Gly Thr Ala Gln Leu
            20                  25                  30 tct ggg cat cgc act gct aga agt cct gga tcg aca ata tgc aaa atg     144
Ser Gly His Arg Thr Ala Arg Ser Pro Gly Ser Thr Ile Cys Lys Met
        35                  40                  45 gcg tgc agg acg gga aac gga cac aag tat ccc ttt tgc aat tgc aga     192
Ala Cys Arg Thr Gly Asn Gly His Lys Tyr Pro Phe Cys Asn Cys Arg
    50                  55                  60 ggg aaa cgg gac gtg gtt tct tca tcg atg gcg gtt tga                 231
Gly Lys Arg Asp Val Val Ser Ser Ser Met Ala Val
65                  70                  75

<210> SEQ ID NO 46
<211> LENGTH: 76
<212> TYPE: PRT
<213> ORGANISM: Conus ferrugineus

<400> SEQUENCE: 46

Met Pro Ser Val Arg Ser Val Thr Cys Cys Cys Leu Leu Trp Met Met
1               5                   10                  15

Leu Ser Val Gln Leu Val Thr Pro Gly Ser Pro Gly Thr Ala Gln Leu
            20                  25                  30

Ser Gly His Arg Thr Ala Arg Ser Pro Gly Ser Thr Ile Cys Lys Met
        35                  40                  45

Ala Cys Arg Thr Gly Asn Gly His Lys Tyr Pro Phe Cys Asn Cys Arg
    50                  55                  60

Gly Lys Arg Asp Val Val Ser Ser Ser Met Ala Val
65                  70                  75

<210> SEQ ID NO 47
<211> LENGTH: 231
<212> TYPE: DNA
<213> ORGANISM: Conus ferrugineus
<220> FEATURE:
<221> NAME/KEY: CDS
<222> LOCATION: (1)..(228)

<400> SEQUENCE: 47 atg ccg tct gtt cgg tct gtg acc tgc tgc tgt ctg ctg tgg atg atg      48
Met Pro Ser Val Arg Ser Val Thr Cys Cys Cys Leu Leu Trp Met Met
1               5                   10                  15 ctc tct gta cag ctg gtt act cct ggc tcc cct gga act gca cag ctg      96
Leu Ser Val Gln Leu Val Thr Pro Gly Ser Pro Gly Thr Ala Gln Leu
            20                  25                  30 tct ggg cag cgc act gct aga agt tct ggg tcg aca gta tgc aag atg     144
Ser Gly Gln Arg Thr Ala Arg Ser Ser Gly Ser Thr Val Cys Lys Met
        35                  40                  45 atg tgc agg ttg gga tac gga cac ttg tat ccc tct tgc gga tgc aga     192
Met Cys Arg Leu Gly Tyr Gly His Leu Tyr Pro Ser Cys Gly Cys Arg
    50                  55                  60 ggg aaa cgg gac gtg gtt tct tca tcg atg gcg gtg tga                 231
Gly Lys Arg Asp Val Val Ser Ser Ser Met Ala Val
65                  70                  75
```

-continued

```
<210> SEQ ID NO 48
<211> LENGTH: 76
<212> TYPE: PRT
<213> ORGANISM: Conus ferrugineus

<400> SEQUENCE: 48

Met Pro Ser Val Arg Ser Val Thr Cys Cys Cys Leu Leu Trp Met Met
1               5                   10                  15

Leu Ser Val Gln Leu Val Thr Pro Gly Ser Pro Gly Thr Ala Gln Leu
            20                  25                  30

Ser Gly Gln Arg Thr Ala Arg Ser Ser Gly Ser Thr Val Cys Lys Met
        35                  40                  45

Met Cys Arg Leu Gly Tyr Gly His Leu Tyr Pro Ser Cys Gly Cys Arg
    50                  55                  60

Gly Lys Arg Asp Val Val Ser Ser Ser Met Ala Val
65                  70                  75

<210> SEQ ID NO 49
<211> LENGTH: 24
<212> TYPE: PRT
<213> ORGANISM: Conus planorbis

<400> SEQUENCE: 49

Phe Pro Arg Pro Arg Ile Cys Asn Leu Ala Cys Arg Ala Gly Ile Gly
1               5                   10                  15

His Lys Tyr Pro Phe Cys His Cys
            20

<210> SEQ ID NO 50
<211> LENGTH: 19
<212> TYPE: PRT
<213> ORGANISM: Conus planorbis

<400> SEQUENCE: 50

Cys Asn Leu Ala Cys Arg Ala Gly Ile Gly His Lys Tyr Pro Phe Cys
1               5                   10                  15

His Cys Arg

<210> SEQ ID NO 51
<211> LENGTH: 18
<212> TYPE: PRT
<213> ORGANISM: Conus planorbis

<400> SEQUENCE: 51

Cys Asn Leu Ala Cys Arg Ala Gly Ile Gly His Lys Tyr Pro Phe Cys
1               5                   10                  15

His Cys
```